(12) United States Patent
Firnges et al.

(10) Patent No.: US 8,058,264 B2
(45) Date of Patent: Nov. 15, 2011

(54) PHARMACEUTICAL COMPOSITIONS COMPRISING CB1 CANNABINOID RECEPTOR ANTAGONISTS AND POTASSIUM CHANNEL OPENERS FOR THE TREATMENT OF OBESITY AND RELATED CONDITIONS

(75) Inventors: Michael Firnges, Barsinghausen (DE); Peter-Colin Gregory, Hanover (DE); Jochen Antel, Münder (DE); Josephus Hubertus Maria Lange, Almere (NL); Harald Waldeck, Isernhagen (DE)

(73) Assignee: Abbott Products GmbH, Hanover (DE)

( * ) Notice: Subject to any disclaimer, the term of this patent is extended or adjusted under 35 U.S.C. 154(b) by 1397 days.

(21) Appl. No.: 11/257,056

(22) Filed: Oct. 25, 2005

(65) Prior Publication Data

US 2006/0128673 A1    Jun. 15, 2006

Related U.S. Application Data

(60) Provisional application No. 60/621,077, filed on Oct. 25, 2004, provisional application No. 60/651,625, filed on Feb. 11, 2005.

(30) Foreign Application Priority Data

Oct. 25, 2004 (EP) .................................... 04105265

(51) Int. Cl.
*A01N 33/26* (2006.01)
*A61K 31/535* (2006.01)

(52) U.S. Cl. .................... 514/150; 514/222.8
(58) Field of Classification Search ................. 514/150, 514/222.8
See application file for complete search history.

(56) References Cited

U.S. PATENT DOCUMENTS

| | | | |
|---|---|---|---|
| 4,070,365 A | 1/1978 | Van Daalen et al. |
| 4,156,007 A | 5/1979 | Van Daalen et al. |
| 4,174,393 A | 11/1979 | Van Daalen et al. |
| 4,358,602 A | 11/1982 | Umezawa et al. |
| 4,598,089 A | 7/1986 | Hadvary et al. |
| 6,267,952 B1 | 7/2001 | Mandeville, III et al. |
| 6,344,474 B1 | 2/2002 | Maruani et al. |
| 6,352,692 B1 | 3/2002 | Mandeville, III et al. |
| 6,352,949 B1 | 3/2002 | Willems et al. |
| 6,476,060 B2 | 11/2002 | Lange et al. |
| 6,558,657 B1 | 5/2003 | Mandeville, III et al. |
| 6,572,850 B1 | 6/2003 | Mandeville, III et al. |
| 6,624,161 B2 | 9/2003 | Hodson et al. |
| 6,900,233 B2 | 5/2005 | Schoenafinger et al. |
| 7,037,944 B2 | 5/2006 | Piot-Grosjean et al. |
| 7,148,258 B2 | 12/2006 | Piot-Grosjean et al. |
| 2002/0091114 A1 | 7/2002 | Piot-Grosjean et al. |
| 2003/0114495 A1 | 6/2003 | Finke et al. |
| 2003/0181433 A1 | 9/2003 | Schoenafinger et al. |
| 2003/0236288 A1 | 12/2003 | Schoenafinger et al. |
| 2004/0106800 A1 | 6/2004 | Lange et al. |
| 2004/0235854 A1 | 11/2004 | Kruse et al. |
| 2004/0248944 A1 | 12/2004 | Kruse et al. |
| 2005/0054679 A1 | 3/2005 | Kruse et al. |
| 2005/0080125 A1* | 4/2005 | Antel et al. ................. 514/406 |
| 2006/0258709 A1 | 11/2006 | Piot-Grosjean et al. |
| 2008/0058381 A1 | 3/2008 | Piot-Grosjean et al. |

FOREIGN PATENT DOCUMENTS

| | | |
|---|---|---|
| DE | 25 29 689 A1 | 1/1976 |
| DE | 31 09 335 A1 | 3/1982 |
| EP | 0 021 506 A2 | 1/1981 |
| EP | 0 129 748 A1 | 1/1985 |
| EP | 0 138 280 A2 | 4/1985 |
| EP | 0 377 457 A1 | 7/1990 |
| FR | 2 814 678 A1 | 4/2002 |
| WO | WO 96/03388 A1 | 2/1996 |
| WO | WO 96/03392 A1 | 2/1996 |
| WO | WO 99/34786 A2 | 7/1999 |
| WO | WO 00/40247 A1 | 7/2000 |
| WO | WO 00/40569 A1 | 7/2000 |
| WO | WO 00/69848 A1 | 11/2000 |
| WO | WO 01/00205 A1 | 1/2001 |
| WO | WO 01/29007 A1 | 4/2001 |
| WO | WO 01/70700 A1 | 9/2001 |

(Continued)

OTHER PUBLICATIONS

Couper et al. Recent advances in therapy of diabetes. MJA vol. 179, Oct. 2003, pp. 441-447.* Younis et al. The prevention of type 2 diabetes mellitus: recent advances. Q J Med 2004; 97: 451-455.*
Hansen et al. Inhibition of insulin secretion as a new drug target in the treatment of metabolic disorders. Current Medicinal Chemistry, 2004, 11, 1595-1615.*
Couper et al. Recent advances in therapy of diabetes. MJA 2003; 179: 441-447.*
Robertson et al. "Update on diabetes diagnosis and management" JADA, vol. 134, Oct. 2003.*
A. Edgar, et al., "Photostimulated luminescence in a rare earth-doped fluorobromozirconate glass ceramic" Applied Physics Letters,(1999) vol. 75; No. 16 pp. 2386-2388.

(Continued)

*Primary Examiner* — Sreeni Padmanabhan
*Assistant Examiner* — Renee Claytor
(74) *Attorney, Agent, or Firm* — Finnegan, Henderson, Farabow, Garrett & Dunner, L.L.P.

(57) ABSTRACT

Described is a novel combination therapy for diabetes mellitus type I and/or for obesity and its concomitant and/or secondary diseases or conditions, in particular the metabolic syndrome and/or syndrome X, and/or diabetes mellitus type II, by administering a combination of at least one $K_{ATP}$ channel opener as a first active agent and at least one $CB_1$ cannabinoid receptor antagonist as a second active agent. The invention is further directed to such novel combination therapy wherein a dually acting compound with combined $K_{ATP}$ channel opening and $CB_1$ antagonistic properties is used. The invention also relates to novel pharmaceutical compositions comprising $K_{ATP}$ channel openers and $CB_1$ antagonists and the use of said pharmaceutical compositions in the treatment, delayed progression, delayed onset of and/or inhibition of diabetes mellitus type 1, and the prophylaxis and treatment, of obesity as well as the prophylaxis, treatment, delayed onset and/or inhbition of its concomitant and/or secondary diseases or conditions, in particular the metabolic syndrome and/or syndrome X, and/or diabetes mellitus type II, in mammals and humans. The invention is further directed to such novel pharmaceutical compositions comprising a dually acting compound with combined $K_{ATP}$ channel opening and $CB_1$ antagonistic properties.

25 Claims, No Drawings

FOREIGN PATENT DOCUMENTS

| WO | WO 02/28346 A2 | 4/2002 |
|---|---|---|
| WO | WO 02/076949 A1 | 10/2002 |
| WO | WO 03/007887 A2 | 1/2003 |
| WO | WO 03/026647 A1 | 4/2003 |
| WO | WO 03/026648 A1 | 4/2003 |
| WO | WO 03/027076 A2 | 4/2003 |
| WO | WO 03/039451 A2 | 5/2003 |
| WO | WO 03/040107 A1 | 5/2003 |
| WO | WO 03/043619 A1 | 5/2003 |
| WO | WO 03/051851 A1 | 6/2003 |
| WO | WO 03/063781 A2 | 8/2003 |
| WO | WO 03/064423 A1 | 8/2003 |
| WO | WO 03/072098 A1 | 9/2003 |
| WO | WO 03/072555 A1 | 9/2003 |
| WO | WO 2004/012727 A1 | 2/2004 |
| WO | WO 2004/026301 A1 | 4/2004 |
| WO | WO 2004/058255 A1 | 7/2004 |

OTHER PUBLICATIONS

S. Schweizer, "Physic and Current Understanding of X-Ray Storage Phosphors" Phys. Stat. Sol. (a)(2001) vol. 187; No. 2, pp. 335-393.

Gang Chen, et al., "ZBLAN-based X-ray storage phosphors and scintillators for digital X-ray imaging" Medical Imaging (2005)Proc. of SPIE vol. 5745 pp. 1351-1358.

Stefan Schweizer, et al., "Photostimulated Luminescence in Eu-doped Fluorochlorozirconate glass ceramics" Applied Physic Letters, (2003) vol. 83, No. 3 pp. 449-451.

Stefan Schweizer, et al., "Photostimulated luminescence from fluorochlorozirconate glass ceramics and the effect of crystallite size" J. of Applied Physics(2005) 97.083522.

Yoshihiro Izumi, et al., "Solid-State X-Ray Imagers" MRS Bulletin (2002) pp. 889-893.

K.H. Abel, et al., "Scintillating Glass Fiber Neutron Sensors: I Production and Optical Characterization" PNL-SA-23095.

Akaji et al., "Efficient Coupling of α, α-Dimethyl Amino Acid Using a New Chloro Imidazolidium Reagent, CIP," Tet. Lett., 35:3315-3318 (1984).

Albericio et al., "On the Use of PyAOP, a Phosphonium Salt Derived from HOAt, in Solid-Phase Peptide Synthesis," Tet. Lett., 38:4853-4856 (1997).

Arslanian, S., "Type 2 Diabetes in Children: Clinical Aspects and Risk Factors," Horm. Res., 57 Suppl. 1:19-28 (2002).

Barth, F., "Cannabinoid Receptor Agonists and Antagonists," Exp. Opin. Ther Patents, 1998, 8(3), 301-313.

Beers et al., The Merck Manual of Diagnosis and Therapy, Section 19—Pediatrics, pp. 2254-2258 (17th Ed. 1999).

Bodanszky et al., "The Practice of Peptide Synthesis," Springer-Vertag, New York, 2nd ed., 1994.

Clerin et al., "Heterocyclisation des α-acylaminoamides. III. Proprietes des amino-5 Oxazoles," Bull. Soc. Chim. F., 1-2:211-217 (1974).

Consroe, Paul, "Brain Cannabinoid Systems as Targets for the Therapy of Neurological Disorders." Neurobiology of Diseases, 1998, 5:534-551, 1998.

Copending U.S. Appl. No. 10/929,377, filed Aug. 31, 2004.
Copending U.S. Appl. No. 10/933,487, filed Sep. 3, 2004.
Copending U.S. Appl. No. 10/969,840, filed Oct. 22, 2004.
Copending U.S. Appl. No. 11/005,486, filed Dec. 7, 2004.

Czollner et al., "Synthesis of New 1,5-Diphenyl-3-1H-1,2,4-triazoles Substituted with H-, Alkyl, or Carboxyl Groups at C-3," Arch. Pharm. (Weinheim), 323:225-227 (1990).

Deckelbaum et al., "Childhood Obesity: The Health Issue," 2001; Obesity Research; 9(Suppl. 4): 239S-243S.

Derwent Abstract for DE 25 29 689, dated Jan. 29, 1976.

Di Marzo et al., "Leptin-regulated endocannabinoids are involved in maintaining food intake," Nature, vol. 410, pp. 822-825, 2001.

Di Marzo et al., "A Structure/Activity Relationship Study on Arvanil, an Endocannabinoid and Vinilloid Hybrid," The Journal of Pharmacology and Experimental Therapeutics, 2002, pp. 984-991, vol. 300, No. 3.

Directive 2001/20/EC of the European Parliament and of the Counsel of Apr. 4, 2001 on the approximation of the laws, regulations and administrative provisions of the Member States relating to the implementation of good clinical practice in the conduct of clinical trials on medicinal products for human use. Official Journal of the European Communities, May 1, 2001, pp. L121/34-L121/44.

Dove, A., "Biotech Weighs Up the Options in Obesity," Nature Biotech. 19:25-28 (2001).

Draft Guidance for Industry Developing Products for Weight Management, US Department of Health & Human Services, Food and Drug Administration, Center for Drug Evaluation and Research, Feb. 2007, Revision 1, pp. 1-16.

Dutta, A. et al., "The Synthesis and Pharmacological Evaluation of the Cannabinoid Antagonist SR 141716A," Med. Chem. Res. 5:54-62 (1994).

Dyck et al., "Potent Imidazole and Triazole CB1 Receptor Antagonists Related to SR141716," Bioorg. Med. Chem. Lett. 14:1151-1154 (2004).

Ebbeling, C.B. et al., "Childhood Obesity: Public-Health Crisis, Common Sense Cure," Lancet 360:473-482 (2002).

Eicher et al., The Chemistry of Heterocycles, Chapter 5: Five-Membered Heterocycles, part 5.46 "1,2,4-Triazole," pp. 208-212, Stuttgart (1995).

Elnagdi et al., "Studies with Polyfunctionally Substituted Heteroaromatics: 2-Phenyl-4-p-Tolylhydrazono-2-oxazoline-5-one as a Precusor for the Synthesis of Substituted 1,2,4-Triazoles and Pyridines," Heteroatom Chem. 6(6):589-592 (1995).

Felder, C. C. et al. "Comparison of the Pharmacology and Signal Transduction of the Human Cannabinoid CB1 and CB2 Receptors," Molecular Pharmacology, 1995, 48: 443-450.

Felder, C. et al., "LY320135, A Novel Cannabinoid CB1 Receptor Antagonist, Unmasks Coupling of the CB1 Receptor to Stimulation of cAMP Accumulation," J. Pharmacol. Exper. Therap., 284(1):291-297 (1998).

Gerdemn et a., "CB1 Cannabiid Receptors Re Critical for Induction of Striatal Long Term Depression," Database Biosis Online Biosciences Information Service, Meeting Abstract, 31st Annual Meeting of the Society for Neuroscience, Nov. 10-15, 2001.

Greenberg, D., "Cannainoids and Neuroprotection in Stroke, "Drug News Perspect. 12(8):458-462 (1999).

Guideline on Clinical Evaluation of Medicinal Products Used in Weight Control, Addendum on Weight Control in Children. European Medicines Agency, Nov. 15, 2007, EMEA/CHMP/EWP/517497/2007, pp. 1-5.

Halford et al., "Pharmacology of Appetite Suppression," Progress in Drug Research Switzerland 54:25-58 (2000).

Harhash et al., "Reactions of 2-Aryl-4-arylhydraono-oxazolin-5-ones with Acid Amides & Diamines," Ind. J. Chem. 14B:268-272 (1976).

Hassan et al., "Design and Synthesis of Some New 1H-1,2,4-Triazoles of Potential Anti-inflammatory and Analgesic Activities," Bull. Pharma. Sci. 17(Part 1):27-39 (1994).

Herremans et al., "SLV319, A Molecule with Cannabinoid CB1 Receptor Antagonist Properties in vitro and in vivo," Program No. 783.17, Society for Neuroscience Abstract Viewer and Itinerary Planner, Washington, DC (2002) online. (Abstract only.).

Hillard, C. et al., "Synthesis and Characterization of Potent and Selective Agonists of the Neuronal Cannabinoid Receptor (CB1)," J. Pharmacology & Exp. Therapeutics, 1999, vol. 289, No. 3, 1427-1433.

Hosohata, K. et al., "AM630 Is a Competitive Cannabinold Receptor Antagonist in the Guinea Pig Brain," Life Sci. 61(9): PL 115-118 (1997).

International Search Report for PCT/EP2004/051961, mailed Nov. 5, 2004.

Jagerovic et al., "A Novel Class of Heterocyclic Cannabinoids: Design, Preparation, in vitro and in vivo Studies of 1,2,4-Triazoles," Drugs Fut., 27(Suppl.A):XVII Int. Symp. On Medicinal Chemstry, pp. 271, P284 (2002).

Kanyonyo, M. et al., "3-Alkyl-(5,5'-Diphenyl)Imidazolidinediones as New Cannabinoid Receptor Ligands," Biorg. & Med. Chem. Lett. 9:2233-2236 (1999).

Kirkham, T., "Endogenous Cannabinoids: a new target in the treatment of obesity," Am. J. Physiol. Regul. Integr. Comp. Physiol., 2003, vol. 284, R343-R344.

Lan, R. et al., "Structure-Activity Relationship of Pyrazole Derivatives as Cannabinoid Receptor Antagonists," J. Med. Chem. 42:769-776 (1999).
Landsman, R. et al., SR141716A Is an Inverse Agonist at the Human Cannabinoid CB, Receptor,: Eur. J. Pharmacol., 344:R1-R2 (1997).
Lange et al., "Synthesis, Biological Properties, and Molecular Modeling Investigations of Novel 3,4-Diarylpyrazolines as Potent and Selective CB1 Cannabinoid Receptor Antagonists," J. Med. Chem. 47:627-643 (2003).
Levin et al., "An Alternative Procedure for the Aluminum-Mediated Conversion of Esters to Amides," Synth. Comm., 12(13):989-993 (1982).
Matsuda, Lisa A. et al., Cannabinoid Receptors, Chapter 4: "Molecular Biology of the Cannabinoid Receptor," Academic Press Limited, 1995, pp. 117-143.
Matthews, W. et al., "Synthesis of [18F] SR144385: A Selective Radioligand for Positron Emission Tomographic Studies of Brian Cannabinoid Receptors," J. Labelled Cpd. Radiopharm., 42:589-596 (1999).
Mechoulam, R et al., "Endocannabinoids," Eur. J. Pharmacol., 359:1-18 (1998).
Mechoulam, R. et al., "Towards Cannabinoid Drugs—Revisited," Prog. Med. Chem., 35:199-243 (1998).
Mechoulam, R. et al., "Towards Cannabinoid Drugs," Prog. Med. Chem., 24:159-207 (1987).
Molnar, "New drug policy in childhood obesity," International Journal of Obesity (2005), 29, S62-65.
Munro, Sean et al., "Molecular Characterization of a Peripheral Receptor for Cannabinoids." Nature, 1993, vol. 365, pp. 61-65.
Mutoh et al., "Panclicins, Novel Pancreatic Lipase Inhibitors: I. Taxonomy, Fermentation, Isolation, and Biological Activity," J. Antibiotics, 47(12):1369-1375 (1994).
Nakamura-Palacios, E. et al., "The Pharmacology of SR 141716A: A Review," CNS Drug Rev. 5(1):43-58 (1999).
Nasrallah, H., "A Review of the Effect of Atypical Antipsychotics on Weight," Psychoneuroendocrinology, 28:83-96 (2003).
Ochi et al., "The Analgesic Effect Profile of FR 122047, a Selective Cyclooxygenase-1 Inhibitor, in Chemical Nociceptive Models," Eu. J. Pharmacol., 391:49-54 (2000).
Office Action dated Jul. 7, 2009, in copending U.S. Appl. No. 10/969,840.
Office Action mailed Jan. 23, 2009, in copending U.S. Appl. No. 10/969,840.
Office Action mailed Jun. 23, 2008, in copending U.S. Appl. No. 10/929,377.
Office Action mailed May 28, 2008, in copending U.S. Appl. No. 10/933,487.
Office Action mailed May 29, 2008, in copending U.S. Appl. No. 10/969,840.
Office Action mailed Nov. 19, 2007, in copending U.S. Appl. No. 10/933,487.
Office Action mailed Oct. 22, 2008, in copending U.S. Appl. No. 11/005,486.
Office Action mailed Sep. 14, 2007, in copending U.S. Appl. No. 10/929,377.
Office Action mailed Apr. 14, 2009, in copending U.S. Appl. No. 10/929,377.
Office Action mailed Feb. 23, 2009, in copending U.S. Appl. No. 10/933,487.
Office Action mailed Apr. 29, 2009, in copending U.S. Appl. No. 11/005,486.
Office Action mailed Oct. 5, 2009, in copending U.S. Appl. No. 11/005,486.
Partial European Search Report for EP 03 01 9939, dated Jan. 19, 2004.
Partial European Search Report for EP 03 10 3961, dated Mar. 18, 2004.
Partial European Search Report for EP 03 10 3967, dated Jul. 29, 2004.
Perio, A. et al., "Central Mediation of the Cannabinoid Cue: Activity of a Selective CB1 Antagonist, SR 141716A," Behavioural Pharmacology, 1996, pp. 65-71, vol. 7.
Pertwee, R., "Cannabinoid receptor ligands: clinical and neuropharmacological considerations relevant to future drug discovery and development," Exp. Opin. Invest. Drugs, 1996, 5(10), 1245-1253.
Pertwee, R., "Pharmacology of Cannabinoid Receptor Ligands," Current Med. Chem., 6:635-664 (1999).
Pop, Emil, "Developing Cannabinoids as Potential Central Nervous System Agents," Current Opinion in CPNS Investigational Drugs, 1999, 1(5):587-596.
Rosenbloom, A.L., "Increasing Incidence of Type 2 Diabetes in Children and Adolescents: Treatment Considerations." Pediatric Drugs 4(4):209-221 (2002).
Sawdey, G., "Rearrangement of 4-Arylazo-2-phenyloxazolin-5-ones: A New Synthesis of 1H-1,2,4-Triazoles," J. Am. Chem. Soc., 79:1955-1956 (1957).
Silink, M., "Childhood Diabetes: A Global Perspective," Horm. Res., 57(Suppl. 1):1-5 (2002).
Sorof et al., "Obesity Hypertension in Children: A Problem of Epidemic Proportions," Hypertension, 40:441-447 (2002).
Spurgeon, D., "Childhood Obesity in Canada Has Tripled in Past 20 Years," BMJ 324(7351): 1416 (2002), Health Care in Canada 2000.
Tanaka et al., "Antiplatelet Agents Based on Cyclooxygenase Inhibition without Ulceroenesis. Evaluation and synthesis of 4,5-bis(4-methoxyphenyl)-2-substituted Thiazoles," J. Med. Chem., 37:1189-1199 (1994).
Thearle et al., "Obesity and Pharmacologic Therapy," Endocrin. Metab. Clin. N. Am., 32:1005-1024 (2003).
Trillou, R. et al., "Anti-obesity effect of SR141716, a CB1 receptor antagonist, in diet-induced obese mice," Am. J. Physiol. Regul. Integr. Comp. Physiol., 2003, vol. 284, R345-R353.
Wiley et al., "Novel Pyrazole Cannabinoids: Insights into CB1 Receptor Recognition and Activation," J. Pharmacol. Exper. Ther., 296:1013-1022 (2001).
Williams, C.M. et al., "Reversal of Δ9-THC hyperphagia by SR141716 and naloxone but not dexfenfluramine," Pharmacology, Biochemistry and Behavior, 2002, vol. 71, 341-348.
Zimmermann, U.T. et al., "Epidemiology, Implications and Mechanisms Underlying Drug-Induced Weight Gain in Psychiatric Patients," J. Psychiatric Res., 37(3): 193-220 (2003).
Alemzadeh, R. et al., "Modification of Insulin Resistance by Diazoxide in Obese Zucker Rats," Endocrinology, 1993, 133(2): 705-712.
Bloomgarden, Z.T., "American Diabetes Association Annual Meeting 1998, More on the Treatment of Type 2 Diabetes," Diabetes Care, 1999, 22(2): 357-361.
Carr, R.D. et al., "NN414, a SUR1/Kir6.2-Selective Potassium Channel Opener, Reduces Blood Glucose and Improves Glucose Tolerance in the VDF Zucker Rat," Diabetes, 52: 2513-2518.
Coghlan, M.J. et al., "Recent Developments in the Biology and Medicinal Chemistry of Potassium Channel Modulators: Update from a Decade of Progress," Journal of Medicinal Chemistry, 2001, 44(11): 1627-1653.
Hansen, J.B. et al., "Inhibition of Insulin Secretion as a New Drug Target in the Treatment of Metabolic Disorders," Current Medicinal Chemistry, 2004, 11: 1595-1615.
Lebrun, P. et al., "$K_{ATP}$ Channel Openers: Tissue Selectivity of Original 3-Alkylaminopyrido- and 3-Alkylaminobenzothiadiazine 1,1-Dioxides," Biochemical Pharmacology, 2008, 75: 468-475.
Tagmose, T.M. et al., "Arylcyanoguanidines as Activators of Kir6.2/SUR1 $K_{atp}$ Channels and Inhibitors of Insulin Release," Journal of Medicinal Chemistry, 2004, 47: 3202-3211.

* cited by examiner

PHARMACEUTICAL COMPOSITIONS COMPRISING CB1 CANNABINOID RECEPTOR ANTAGONISTS AND POTASSIUM CHANNEL OPENERS FOR THE TREATMENT OF OBESITY AND RELATED CONDITIONS

The present invention relates to a novel combination therapy for diabetes mellitus type I and/or for obesity and its concomitant and/or secondary diseases or conditions, in particular the metabolic syndrome and/or syndrome X, and/or diabetes mellitus type II, by administering a combination of at least one $K_{ATP}$ channel opener as a first active agent and at least one $CB_1$ cannabinoid receptor antagonist as a second active agent. The invention is further directed to such novel combination therapy wherein a dually acting compound, said compound comprising combined $K_{ATP}$ channel opening and $CB_1$ antagonistic properties, is used. Thus, the invention also relates to novel pharmaceutical compositions comprising $K_{ATP}$ channel openers and $CB_1$ antagonists and the use of said pharmaceutical compositions in the treatment, delayed progression, delayed onset of and/or inhibition of diabetes mellitus type I, and the prophylaxis and treatment, of obesity as well as the prophylaxis, treatment, delayed onset and/or inhibition of its concomitant and/or secondary diseases or conditions, in particular the metabolic syndrome and/or syndrome X, and/or diabetes mellitus type II, in mammals and humans. A particular embodiment of the present invention relates to the use of dually acting compounds, said compounds comprising combined $K_{ATP}$ channel opening and $CB_1$ antagonistic properties, in the novel combination therapy. Thus, the present invention is further directed to novel pharmaceutical compositions comprising a dually acting compound, said compound comprising combined $K_{ATP}$ channel opening and $CB_1$ antagonistic properties. Another particular embodiment of the present invention relates to a novel therapy for patients with established obesity, thereby delaying or preventing onset or aggravation of concomitant and/or secondary diseases or conditions associated with obesity like the metabolic syndrome and/or syndrome X, in particular diabetes mellitus type II (hereinafter referred to as "type II diabetes") and/or insulin resistance. Another particular embodiment of the present invention is directed to the weight-loss independent treatment of diabetes type I or diabetes type II patients by administering to such patients either a combination comprising $K_{ATP}$ channel openers and $CB_1$ antagonists or a dually acting compound, said compound comprising combined $K_{ATP}$ channel opening and $CB_1$ antagonistic properties. The invention also relates to kits comprising in separate containers in a single package pharmaceutical dosage forms for use in combination, the kit comprises, in one separate container a pharmaceutical dosage form comprising at least one $K_{ATP}$ channel opener and in a second separate container a pharmaceutical dosage form comprising at least one $CB_1$ antagonist, or in one separate container a pharmaceutical dosage form comprising a dually acting compound, said compound comprising combined $K_{ATP}$ channel opening and $CB_1$ antagonistic properties.

Obesity according to the present invention is meant to comprise any increase in body fat that results in increased bodyweight, preferably comprising but not limited to the medical definition of obesity. Thus, in accordance with the invention, obesity also comprises non-medical, e.g. cosmetic overweight. The invention thus also relates to non-medical weight loss, such as cosmetic weight loss and includes improving bodily appearance in general. In a more narrowed sense, obesity is usually understood to denominate a body weight more than 20% above the ideal body weight. Even in this more narrowed sense, obesity is a major health concern in Western societies. It is estimated that about 97 million adults in the United States are overweight or obese. Obesity is largely the result of a positive energy balance as a consequence of increased ratio of caloric intake to energy expenditure. The molecular factors regulating food intake and body weight are incompletely understood, but several genetic factors have been identified.

Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, generally include hypertension; type II diabetes mellitus; elevated plasma insulin concentrations; insulin resistance; dyslipidemias; hyperlipidemia; endometrial, breast, prostate and colon cancer; osteoarthritis; respiratory complications, such as obstructive sleep apnea; cholelithiasis; gallstones; arteriosclerosis; heart disease; abnormal heart rhythms; and heart arrythmias. Obesity is further associated with premature death and with a significant increase in mortality and morbidity from stroke, myocardial infarction, congestive heart failure, coronary heart disease, and sudden death.

Obesity is often treated by encouraging patients to lose weight by reducing their food intake or by increasing their exercise level and therefore increasing their energy output. A sustained weight loss of 5% to 10% of body weight has been shown to improve the co-morbidities associated with obesity, such as diabetes and hypertension, and can lead to improvement of obesity-related conditions such as osteoarthritis, sleep apnea and pulmonary and cardiac dysfunction.

Weight loss drugs that are currently used in monotherapy for the treatment of obesity have limited efficacy and significant side effects. During chronic treatment periods of greater than six months the efficacy of most agents decreases yielding no more than 10% body weight loss compared to control. Obese humans can easily mass over 150 kg and would, therefore, need to lose more than 50% of their body mass to return to a normal body mass.

Diabetes mellitus type I is usually diagnosed in children and young adults, and was previously known as juvenile diabetes. In type 1 diabetes, the body does not produce insulin. Insulin is necessary for the body to be able to use sugar which is the basic fuel for the cells in the body. Insulin takes the sugar from the blood into the cells. Type 1 diabetes is serious, as many risks are increased for many serious complications. A lack of insulin leads to hyperglycaemia, which if untreated, over time leads to neuropathy and vascular damage and increases the risks for further complications such as eye damage or even blindness (retinopathy), kidney damage (nephropathy), skin complications, foot disease and/or gastroparesis. Furthermore, life-threatening diabetic ketoacidosis can develop if steps are not taken to control the hyperglycaemia and lack of insulin, as the body seeks to obtain energy supplies. Prevention of hyperglycaemia is achieved by injection or infusion of insulin. On the other hand, insulin overdosage can lead to hypoglycaemia, loss of consciousness or seizure so that it is imperative to maintain a good control over blood insulin and glucose levels. Treatment of patients in the pre-diabetic state or in the early period with still functional pancreas to improve insulin sensitivity together with pancreatic beta cell rest offers the hope of requiring lower insulin doses and of delaying the onset or the progression of the disease.

Therefore, it was an objective of the present invention to provide a more effective and/or more selective therapy for diabetes mellitus type I and/or for obesity and its concomitant and/or secondary diseases or conditions, in particular the metabolic syndrome and/or syndrome X, and/or diabetes mellitus type II.

It has now surprisingly been found that a novel combination therapy which comprises administering a combination of at least one $K_{ATP}$ channel opener as a first active agent and at least one $CB_1$ antagonist as a second active agent to a patient in need thereof can provide an effective and/or selective therapy for diabetes mellitus type I and/or for obesity and its concomitant and/or secondary diseases or conditions, in particular the metabolic syndrome and/or syndrome X and/or diabetes mellitus type II. More specifically, due to the long term effect of therapy with a $K_{ATP}$ channel opener, this new combination therapy is particularly suited for the prophylaxis of metabolic syndrome and/or syndrome X in patients exposed to an elevated risk of acquiring such diseases, like patients with established obesity. However, due to its direct effect on glucose metabolism, the novel combination therapy according to the invention is also well suited to treat type II diabetes and insulin resistance in patients without concomitant obesity.

Potassium channels play an important role in membrane potential. Among the different types of potassium channels are the ATP-sensitive ($K_{ATP}$-) channels, which are regulated by changes in the intracellular concentration of nucleotides. The $K_{ATP}$-channels have been found in cells from various tissues such as cardiac cells, pancreatic-cells, skeletal muscles, smooth muscles, central neurons, adipocytes and adenohypophysis cells. The channels have been associated with diverse cellular functions for example hormone secretion (insulin from pancreatic beta-cells, growth hormone and prolactin from adenohypophysis cells), vasodilation (in smooth muscle cells), cardiac action potential duration, neurotransmitter release in the central nervous system and lipid metabolism. $K_{ATP}$-channels exist as octameric complexes of the sulfonylurea receptor (SUR) and the poreforming inwardly rectifying potassium channel (Kir) in a 4+4 stoichiometry. Activity of the channels is regulated by intracellular nucleotides and by different drugs. For example, MgADP and potassium channel openers stimulate potassium currents. The genes for two closely related sulfonylurea receptors, SUR1 and SUR2, have been cloned. Two different splice variants of SUR2, namely SUR2A and SUR2B have been reported. SUR1 combines with Kir6.2 to form the $K_{ATP}$-channels of pancreatic beta cells and neurones, whereas the cardiac type consists of SUR2A and Kir6.2 and the smooth muscle type of SUR2B and Kir6.1 or Kir6.2.

$K_{ATP}$ channel openers and their potential use in the inhibition of insulin secretion and/or the treatment of metabolic disorders are known e.g. from documents U.S. Pat. No. 6,492, 130; WO 02/00223; WO 02/00665 or from R. D. Carr et al., Diabetes 52 (2003) 2513-2518 (="Carr et al.") or J. B. Hansen et al., Current Medicinal Chemistry 11 (2004) 1595-1615 (="Hansen et al.").

The beneficial role of the specific $K_{ATP}$ channel opener diazoxide in the treatment of i.a. the metabolic syndrome is known e.g. from documents U.S. Pat. Nos. 5,284,845 or 6,197,765 or from R. Alemzadeh et al., Endocrinology 133 (2) (1993) 705-712 or R. Alemzadeh et al., Journal of Clinical Endocrinology and Metabolism 83 (6) (1998) 1911-1915.

$CB_1$ antagonists and their potential use in treating or inhibiting obesity are known e.g. from documents U.S. Pat. Nos. 5,624,941; 6,344,474; WO 01/070700; WO 02/076949; WO 03/026647; WO 03/026648; WO 03/027076; WO 03/078413 and WO 04/026301. A review is given in J. H. M. Lange and C. G. Kruse, Current Opinion in Drug Discovery & Development 7(4) (2004) 498-506.

Some combination treatments for obesity and related conditions are already known e.g. from documents WO 04/034968 or U.S. 2004/0122033.

Further, it has already been known, that 5-(4-chlorophenyl)-1-(2,4-dichlorophenyl)-4-methyl-N-piperidin-1-yl-1H-pyrazole-3-carboxamide (=Acomplia™) is a $CB_1$ antagonist with beneficial effects on i.a. obesity (see e.g. U.S. Pat. No. 6,344,474). It is also known from clinical studies (see e.g. presentations of the "RIO Europe study" at the European Society of Cardiology 2004 Congress, 28. August—01. September 2004 in Munich, Germany) that chronic treatment (e.g. over a period of 1 year) with 5-(4-chlorophenyl)-1-(2,4-dichlorophenyl)-4-methyl-N-piperidin-1-yl-1H-pyrazole-3-carboxamide can improve glucose tolerance and insulin resistance in obese patients. It was not known, however, whether these observed effects were due to metabolic rebalance after weight loss or due to direct and/or acute effects.

In an oral glucose tolerance test (=OGTT) in the fatty Zucker rat and performed in the context of this invention, it has now surprisingly been found that acute administration of 5-(4-chlorophenyl)-1-(2,4-dichlorophenyl)-4-methyl-N-piperidin-1-yl-1H-pyrazole-3-carboxamide (i.e. over a period of 1 day) causes a strong increase in glucose plasma levels and a significantly reduced inhibition of insulin release. These findings would not have been expected for a compound with purely $CB_1$ antagonistic activity. It has therefore subsequently and surprisingly been found that 5-(4-chlorophenyl)-1-(2,4-dichlorophenyl)-4-methyl-N-piperidin-1-yl-1H-pyrazole-3-carboxamide is also a potent opener at the Kir6.2/SUR1 $K_{ATP}$ channel. These $K_{ATP}$ channel opening properties of 5-(4-chlorophenyl)-1-(2,4-dichlorophenyl)-4-methyl-N-piperidin-1-yl-1H-pyrazole-3-carboxamide are more in line with the results of the acute OGTT (see also Carr et al., Hansen et al.). It can therefore be concluded from the above, that the extraordinarily beneficial effects of 5-(4-chlorophenyl)-1-(2,4-dichlorophenyl)-4-methyl-N-piperidin-1-yl-1H-pyrazole-3-carbox-amide on obesity, chronic glucose tolerance and chronic insulin resistance are not only due to its properties as a $CB_1$ antagonist, but that its additional properties as an opener at $K_{ATP}$ channels significantly contribute to its full therapeutic value. It can further be concluded from the foregoing that a therapeutic profile of action comprising combined $K_{ATP}$ channel opening and $CB_1$ antagonistic properties will result in reduced bodyweight due to reduced intake of highly palatable, energy dense food and in improved glucose tolerance, e.g. due to reduced bodyweight as well as by increased insulin sensitivity via improved pancreatic beta cell function due to beta cell rest.

A object of the invention is therefore in a first aspect a pharmaceutical composition comprising pharmacologically effective quantities of each of a) at least one $K_{ATP}$ channel opener as a first active agent and b) at least one $CB_1$ antagonist as a second active agent.

Usually, such pharmaceutical compositions will further comprise at least one additional component chosen from pharmaceutically acceptable auxiliary substances and carriers.

Suitable $K_{ATP}$ channel openers are preferably compounds which have effects as openers at the Kir6.2/SUR1 $K_{ATP}$ channel, at the Kir6.2/SUR2B $K_{ATP}$ channel and/or the Kir6.1/SUR2B $K_{ATP}$ channel. Effective are those compounds which exhibit an $IC_{50}$ value [µmol] of less than 50 in a test for the affinity of the compounds in binding to the sulfonylurea (=SUR) and potassium channel opener site (=KCO) of rat and/or human isoforms of SUR1 and/or SUR2B—e.g. the test model provided below. Compounds with an effect as openers at the Kir6.2/SUR1 $K_{ATP}$ channel, in particular as selective openers at the Kir6.2/SUR1 $K_{ATP}$ channel are preferred. A compound with an effect as opener at the Kir6.2/SUR1 $K_{ATP}$ channel is understood to be selective if its $IC_{50}$ value at the Kir6.2/SUR1 $K_{ATP}$ channel, as measured in the aforementioned binding test, is at most half, more preferred only a quarter, of the $IC_{50}$ value of that same compound at the Kir6.2/SUR2B $K_{ATP}$ channel and/or the Kir6.1/SUR2B $K_{ATP}$ channel. Specific compounds which are suitable as $K_{ATP}$ channel openers according to the invention may be chosen from pinacidil; cromakalim; diazoxide; BPDZ 44; BPDZ 49; BPDZ 62; BPDZ 73; BPDZ 79; BPDZ 83; BPDZ 109; BPDZ 154; BPDZ 216 (=NNC 55-9216); NN414 (all: see e.g. Hansen et al.); NNC 55-0118 (see e.g. T. M. Tagmose et al., J. Med. Chem. 47 (2004) 3202-3211); NNC 55-0462 (see e.g. Hansen et al.), MCC-134 (see e.g. M. J. Coghlan et al., J. Med. Chem. 44 (2001) 1627-1653); losimendan; SR 47063 and WAY 135201. Diazoxide; BPDZ 44; BPDZ 62; BPDZ 73; BPDZ 154; BPDZ 216 (=NNC 55-9216); NN414; NNC 55-0118; NNC 55-0462 and MCC-134 are preferred.

Suitable $CB_1$ antagonists are e.g. those which are useful to treat appetite disorders and/or obesity, e.g. [5-(4-Bromophenyl)-1-(2,4-dichlorophenyl)-4-ethyl-N-(1-piperidinyl)-1H-pyrazole-3-carboxamide]. Further examples of such compounds are described in documents U.S. Pat. Nos. 5,624,941; 6,344,474; 6,509,367; WO 01/032663; WO 01/070700; WO 03/007887; WO 03/015700; WO 03/026647; WO 03/026648; WO 03/027076; WO 03/040107; WO 03/051850; WO 03/051851; WO 03/063781; WO 03/077847; WO 03/078413; WO 03/082190; WO 03/082191; WO 03/082256; WO 03/082833; WO 03/084930; WO 03/084943; WO 03/086288; WO 03/087037; WO 03/088968; WO 04/012671; WO 04/013120; WO 04/026301; WO 04/052864; WO 04/060888; WO 04/060870; WO 058727 and WO 04/058255, WO 05/0076288, the contents of which are herewith incorporated by reference.

Preferred are the $CB_1$ antagonists of general Formula I,

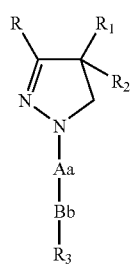

(I)

wherein
$R^4$ is chosen from acetamido, dimethylamino, 2,2,2-trifluoroethyl, phenyl and pyridyl groups and
$R^5$ is chosen from hydrogen, or
$R^4$ and $R^5$ independently of each other are chosen from hydrogen, $C_{1-8}$ branched or unbranched alkyl, and $C_{3-8}$ cycloalkyl groups,
$R^6$ is chosen from hydrogen and $C_{1-3}$ unbranched alkyl groups,
Bb is chosen from sulfonyl and carbonyl groups,
$R^3$ is chosen from benzyl, phenyl, thienyl and pyridyl groups which may be substituted with 1, 2 or 3 substituents Y, which can each be the same or different or $R_3$ is chosen from $C_{1-8}$ branched or unbranched alkyl, and $C_{3-8}$ cycloalkyl groups, or $R_3$ is chosen from pyrrolidinyl, piperidinyl, morpholinyl, 3,4-dihydro-2H[1,4]oxazinyl and naphthyl groups, a prodrug thereof, a tautomer thereof or a pharmaceutically acceptable salt thereof.

More preferred is the compound of Formula I, wherein R is the group 4-chlorophenyl, $R^1$ is phenyl, $R^2$ is hydrogen, Aa is the group (i) wherein $R^4$ is hydrogen and $R^5$ is methyl, Bb is sulfonyl, and $R^3$ is chosen from 4-chlorophenyl, and salts thereof. Best suited are levorotatory enantiomers of compounds of Formula I. Particularly preferred are the compounds chosen from (S)-3-(4-chlorophenyl)-N-[(4-chlorophenyl)sulfonyl]-4,5-dihydro-N'-methyl-4-phenyl-1H-pyrazole-1-carboximidamide; (−)-3-(4-chlorophenyl)-4,5-dihydro-N-methyl-4-phenyl-N'-(1-piperidinylsulfonyl)-1H-pyrazole-1-carboximidamide and (−)-3-(4-chlorophenyl)-4,5-dihydro-4-phenyl-N-methyl-N'-[[4-(trifluoromethyl)phenyl]sulfonyl]-1H-pyrazole-1-carboximidamide. The foregoing compounds are known per se, e.g. from the documents WO 01/70700, WO 02/076949 and/or WO 03/026648.

For example, suitable CB1 antagonists according to the invention can also be compounds of general Formula III,

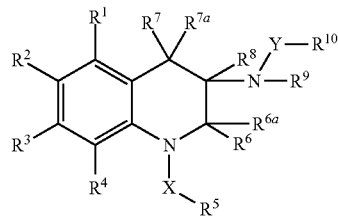

III including all pharmaceutically acceptable salts and stereoisomers, wherein $R^1$ is chosen from hydrogen, alkyl, halo and CN groups;
$R^2$ is chosen from hydrogen, alkyl, alkenyl, alkynyl, cycloalkyl, cycloalkylalkyl, heterocyclyl, heterocycloalkyl, aryl, heteroaryl, arylalkyl, heteroarylalkyl, acyl, halo, $CF_3$, CN, nitro, $OR^{11}$, $NR^{12}R^{12a}$, $COOR^{12}$ and $COONR^{12}R^{12a}$ groups;
$R^3$ is chosen from hydrogen, alkyl, halo and CN groups;
$R^4$ is chosen from hydrogen, alkyl, halo and CN groups;
$R^5$ is chosen from alkyl, alkenyl, alkynyl, cycloalkyl, heterocyclyl, aryl, heteroaryl, $COOR^{13}$ and $CONR^{13}R^{13a}$,halo and CN groups;
$R^6$ and $R^{6a}$ are each independently chosen from hydrogen, alkyl and cycloalkyl groups;
$R^7$ and $R^{7a}$ are each independently chosen form hydrogen, alkyl and cycloalkyl groups;
$R^8$ is chosen from hydrogen and alkyl groups;
$R^9$ is chosen from hydrogen, alkyl, alkenyl, alkynyl, cycloalkyl, cycloalkylalkyl, heterocyclyl, heterocycloalkyl, aryl, heteroaryl, arylalkyl and heteroarylalkyl groups;
$R^{10}$ is chosen from alkyl, alkenyl, alkynyl, cycloalkyl, cycloalkylalkyl, heterocyclyl, heterocycloalkyl, aryl, heteroaryl, arylalkyl and heteroarylalkyl groups;
$R^{11}$ is chosen from hydrogen, alkyl, alkenyl, alkynyl, cycloalkyl, cycloalkylalkyl, heterocyclyl, heterocycloalkyl, aryl, heteroaryl, arylalkyl, heteroarylalkyl, $CHF_2$ and $CF_3$ groups;
$R^{12}$ and $R^{12a}$ are each independently chosen from hydrogen, alkyl, alkenyl, alkynyl, cycloalkyl, cycloalkylalkyl, heterocyclyl, heterocycloalkyl, aryl, heteroaryl, arylalkyl and heteroarylalkyl groups;

or $R^{12}$ and $R^{12a}$ taken together can form cycloalkyl or heterocyclyl groups;

$R^{13}$ and $R^{13a}$ are each independently chosen from hydrogen, alkyl, alkenyl, alkynyl, cycloalkyl, cycloalkylalkyl, heterocyclyl, heterocycloalkyl, aryl, heteroaryl, arylalkyl and heteroarylalkyl groups;

or $R^{13}$ and $R^{13a}$ taken together can form cycloalkyl or heterocyclyl groups;

X is chosen from $(CR_{14}R_{14a})_n$, CO, COO, $S(O)_2$, $SO_2N(R_{12})$ and $CON(R_{12})$ groups;

or $R^5$ and $R^{12}$ taken together can form cycloalkyl or heterocyclyl groups;

Y is chosen from $S(O)_2$, $SO_2N$ $(R_{15})$ and $C(O)C(O)$ groups;

$R^{14}$ and $R^{14a}$ are each independently chosen from hydrogen and alkyl groups;

$R^{15}$ is chosen from hydrogen, alkyl, alkenyl, alkynyl, cycloalkyl, cycloalkylalkyl, heterocyclyl, heterocycloalkyl, aryl, heteroaryl, arylalkyl and heteroarylalkyl groups;

or $R^{10}$ and $R^{15}$ taken together can form cycloalkyl or heterocyclyl groups;

n is an integer of 0, 1 or 2;

with the following provisos:

$R^5$ is not imidazole or substituted imidazole groups;

when X is $(CR_{14}R_{14a})_n$, n is 1, $R^{14}$ is H and $R^{14a}$ is alkyl, $R^5$ is not cycloalkyl, aryl or heteroaryl groups;

when Y is $S(O)_2$, $R^{10}$ is not a seven-membered lactam groups; and when Y is $SO_2N$ (R $^{15}$), neither $R^{10}$ nor $R^{15}$ is a seven-membered lactam groups.

The compounds of Formula III are known from international patent application WO 2005/007628 and can be prepared according to the methods described therein, the entire disclosure of which is incorporated herewith by reference. The substituents and preferred embodiments of the compounds of formula III are as describe in document WO 2005/007628.

Usually a compound can be denominated a $CB_1$ antagonist, if it shows $pA_2$ values of at least 7.0 in the in vitro test for $CB_2$ receptor antagonistic activity described below.

The concomitant diseases of obesity or the secondary diseases thereof which can each be treated with the combinations or compounds according to the invention include in particular metabolic syndrome and/or syndrome X and cardiovascular diseases.

The term "metabolic syndrome" is meant to cover a complex of clinical pictures which—besides central obesity—mainly comprises hypertension, in particular arterial hypertension; insulin resistance, in particular type II diabetes; glucose intolerance; dyslipoproteinaemia, in particular as hypertriglyceridaemia, accompanied by dyslipoproteinaemia occurring with lowered HDL-cholesterol, and also hyperuricaemia, which can lead to gout.

According to information from the American Heart Association, the metabolic syndrome is closely linked to insulin resistance. Some people are genetically predisposed to insulin resistance. Acquired factors, such as excess body fat and physical inactivity, can elicit insulin resistance and the metabolic syndrome in these people. Most people with insulin resistance have central obesity. The biologic mechanisms at the molecular level between insulin resistance and metabolic risk factors are not fully understood and appear to be complex. One group of people at risk for developing metabolic syndrome is those with diabetes who have a defect in insulin action and cannot maintain a proper level of glucose in their blood. Another is people, mainly those with high blood pressure, who are non-diabetic and insulin-resistant but who compensate by secreting large amounts of insulin. This condition is known as hyperinsulinemia. A third group is heart attack survivors who, unlike hypertensives, have hyperinsulinemia without having abnormal glucose levels. The metabolic syndrome has become increasingly common in higher developed countries like the United States, where it is estimated that about 20-25 percent of US adults have it. There are no well-accepted criteria for diagnosing the metabolic syndrome. The criteria proposed by the Third Report of the National Cholesterol Education Program (NCEP) Expert Panel on Detection, Evaluation, and Treatment of High Blood Cholesterol in Adults (Adult Treatment Panel III) are the most current and widely used. According to the ATP III criteria, the metabolic syndrome is identified by the presence of three or more of these following components:

a. Central obesity as measured by waist circumference (Men—Greater than 40 inches; Women—Greater than 35 inches).

b. Fasting blood triglycerides greater than or equal to 150 mg/dL.

c. Blood HDL cholesterol (Men—Less than 40 mg/dL; Women—Less than 50 mg/dL).

d. Blood pressure greater than or equal to 130/85 mmHg.

e. Fasting glucose greater than or equal to 110 mg/dL.

The term "syndrome X" is closely related to the term "metabolic syndrome" and usually is supposed to denominate the identical disease or condition. According to information from the American Heart Association, the term "Syndrome X" refers, however, additionally to a heart condition where chest pain and electrocardiographic changes that suggest ischemic heart disease are present, but where there are no angiographic findings of coronary disease. Patients with cardiac syndrome X also sometimes have lipid abnormalities.

The term "cardiovascular diseases" in conjunction with obesity is usually understood to mean coronary heart disease, which can lead to heart failure; cerebrovascular diseases, which may for example be accompanied by an increased risk of strokes; and peripheral occlusive arterial disease.

Further concomitant and/or secondary diseases of obesity may be gallbladder diseases such as formation of gallstones, sleep apnea syndrome, orthopaedic complications such as osteoarthritis and psychosocial disorders.

In a specific and preferred embodiment of the first aspect of the invention, the pharmaceutical composition may comprise a dually acting compound, said compound comprising combined $K_{ATP}$ channel opening and $CB_1$ antagonistic properties. Examples for those dually acting compounds are 5-(4-chlorophenyl)-1-(2,4-dichlorophenyl)-4-methyl-N-piperidin-1-yl-1H-pyrazole-3-carboxamide, which is e.g. known from documents U.S. Pat. Nos. 5,624,941 and 6,344,474; or 5-(4-chlorophenyl)-4-(2,4-dichlorophenyl)-N-(1-piperidinyl)-thiazole-2-carboxamide of Formula II,

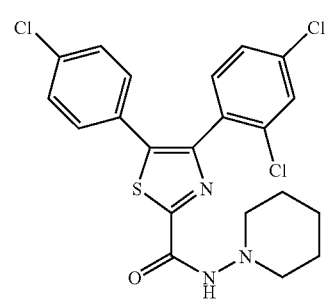

which is e.g. known from document WO 03/078413 and which carries the compound code "S20220095". Other examples for those dually acting compounds are (4S)-3-(4-chlorophenyl)-N'-[(4-chlorophenyl)sulfonyl]-N-methyl-4-phenyl-4,5-dihydro-1H-pyrazole-1-carboximidamide; 5-(4-bromophenyl)-1-(2,4-dichlorophenyl)-4-ethyl-N-piperidin-1-yl-1H-pyrazole-3-carboxamide; 5-(1,1-dimethylheptyl)-2-[(1R,2R,5R)-5-hydroxy-2-(3-hydroxy-propyl)cyclohexyl]-phenol; 5-(4-chlorophenyl)-1-(2,4-dichlorophenyl)-4-methyl-N-piperidin-1-yl-1H-pyrazole-3-carboxamide; N'-(azepan-1-ylsulfonyl)-3-(4-chlorophenyl)-N-methyl-4-phenyl-4,5-dihydro-1H-pyrazole-1-carboximidamide; (2S)-1-[3-(4-chlorophenyl)-4-phenyl-4,5-dihydro-1H-pyrazol-1-yl]-3-(3,4-dichloro-phenyl)-1-oxopropan-2-amine; 3-(4-chloro-phenyl)-N'-[(4-chlorophenyl)sulfonyl]-4-phenyl-N-(pyridin-3-ylmethyl)-4,5-dihydro-1H-pyrazole-1-carboximidamide; (2S)-1-[3-(4-chlorophenyl)-4-phenyl-4,5-dihydro-1H-pyrazol-1-yl]-3-(1H-indol-3-yl)-N-methyl-1-oxopropan-2-amine; 2-[3-(4-chlorophenyl)-4-phenyl-4,5-dihydro-1H-pyrazol-1-yl]-5-ethyl-4,5-dihydro-1,3-oxazole; 3-(4-chlorophenyl)-N-[2-(diethyl-amino)ethyl]-N'-[(diethylamino)sulfonyl]-4-phenyl-4,5-dihydro-1H-pyrazole-1-carbox-imidamide; 3-(4-chlorophenyl)-N-[(4-chlorophenyl)sulfonyl]-N'-(3-hydroxy-2,2-di-methylpropyl)-4-phenyl-4,5-dihydro-1H-pyrazole-1-carboximidamide; 3-(4-chlorophenyl)-N-[2-(dimethyl-amino)ethyl]-4-phenyl-N'-(piperidin-1-ylsulfonyl)-4,5-dihydro-1H-pyrazole-1-carbox-imidamide; 3-(4-chlorophenyl)-N'-[(4-chlorophenyl)sulfonyl]-N-[(1-methylpyrrolidin-3-yl)-methyl]-4-phenyl-4,5-dihydro-1H-pyrazole-1-carboximidamide; 3-(4-chlorophenyl)-N-{[iso-propyl(methyl)amino]sulfonyl}-4-phenyl-4,5-dihydro-1H-pyrazole-1-carbothioamide; 5-(4-bromophenyl)-N-[(4-chlorophenyl)sulfonyl]-1-(2,4-dichlorophenyl)-1H-pyrazole-3-carbox-amide; 5-(4-bromophenyl)-1-(2,4-dichlorophenyl)-1H-pyrazole-3-carbonitrile; 8-chloro-1-(2,4-dichlorophenyl)-N-piperidin-1-yl-1,4,5,6-tetrahydrobenzo[6,7]cyclo-hepta-[1,2-c]pyra-zole-3-carboxamide; 3-(4-chlorophenyl)-N'-[(diethylamino)sulfonyl]4-hydroxy-N-methyl4-phenyl-4,5-dihydro-1H-pyrazole-1-carboximidamide; methyl 3-(4-chloro-phenyl)-N-[(diethylamino)sulfonyl]4-phenyl4,5-dihydro-1H-pyrazole-1-carbimidothioate; 1-[bis(4-chlorophenyl)methyl]-3-[(3,5-difluorophenyl)(methylsulfonyl)methylene]-azetidine; 5-(4-bromophenyl)-1-(2,4-dichlorophenyl)-3-[(Z)-2-(3,5-difluorophenyl)-2-(methylsulfonyl)-vinyl]4-methyl-1H-pyrazole; 4-(4-chlorophenyl)-5-(2,4-dichlorophenyl)-N-piperidin-1-yl-1,3-thiazole-2-carboxamide; 2-{1-[bis(4-chlorophenyl)methyl]azetidin-3-yl}-1,2-benziso-thiazol-3(2H)-one 1,1-dioxide; 5-(4-chlorophenyl)-4-(2,4-dichlorophenyl)-N-piperidin-1-yl-1,3-thiazole-2-carboxamide; 1-(4-bromophenyl)-N-cyclohexyl-2-(2,4-dichlorophenyl)-5-ethyl-1H-imidazole-4-carboxamide; 1-(4-bromophenyl)-2-(2,4-dichlorophenyl)-5-ethyl-N-pentyl-1H-imidazole-4-carboxamide; 5-(4-chlorophenyl)-1-(2,4-dichlorophenyl)-N-pyrrolidin-1-yl-1H-1,2,4-triazole-3-carboxamide; 3-(4-chlorophenyl)-N'-[(4-hydroxypiperidin-1-yl)sulfonyl]-N-methyl-4-phenyl-4,5-dihydro-1H-pyrazole-1-carboximidamide; 3-(4-chloro-phenyl)-N'-[(dimethylamino)sulfonyl]-N-(2-fluoroethyl)-4-phenyl-4,5-dihydro-1H-pyrazole-1-carboximidamide; 1-(4-chlorophenyl)-5-(2,4-dichlorophenyl)-N-piperidin-1-yl-1H-1,2,4-triazole-3-carboxamide; 1-(4-chlorophenyl)-5-(2,4-dichlorophenyl)-N-morpholin-4-yl-1H-1,2,4-triazole-3-carboxamide; 3-(4-chlorophenyl)-4-(3-fluorophenyl)-N-methyl-N'-(piper-idin-1-ylsulfonyl)-4,5-dihydro-1H-pyrazole-1-carboximidamide; 3-(4-chlorophenyl)-N-methyl-N'-(morpholin-4-ylsulfonyl)-4-phenyl-4,5-dihydro-1H-pyrazole-1-carboximidamide; 4-(4-chlorophenyl)-N-cyclohexyl-5-(2,4-dichlorophenyl)-1-methyl-1H-imidazole-2-carbox-amide; 5-(4-chlorophenyl)-N-cyclohexyl-4-(2,4-dichlorophenyl)-1-methyl-1H-imidazole-2-carboxamide; 1-(4-chlorophenyl)-2-(2,4-dichlorophenyl)-N,N-diethyl-1H-imidazole-4-carboxamide; 5-(4-chlorophenyl)-1-(2,4-dichlorophenyl)-N-piperidin-1-yl-4,5-dihydro-1H-pyrazole-3-carboxamide; 3-(4-chlorophenyl)-N'-[(4-chlorophenyl)sulfonyl]-N-methyl4-pyridin-3-yl-4,5-dihydro-1H-pyrazole-1-carboximidamide; 1-(4-chlorophenyl)-5-phenyl-N-piperidin-1-yl-4,5-dihydro-1H-pyrazole-3-carboxamide; 1-(4-chlorophenyl)-5-phenyl-4,5-dihydro-1H-pyrazole-3-carboximidamide; 1-(4-chlorophenyl)-2-(2,4-dichlorophenyl)-N-(4-hydroxycyclohexyl)-5-methyl-1H-imidazole-4-carboxamide; N-azepan-1-yl-1-(4-chloro-phenyl)-2-(2,4-dichlorophenyl)-5-methyl-1H-imidazole-4-carboxamide; 2-(2,5-dichloro-phenyl)-5-ethyl-1-phenyl-N-piperidin-1-yl-1H-imidazole-4-carboxamide; N-cyclohexyl-2-(1,5-dimethyl-1H-pyrrol-2-yl)-5-ethyl-1-phenyl-1H-imidazole-4-carboxamide; 1-(4-chloro-phenyl)-N-methyl-5-phenyl-N'-(piperidin-1-ylsulfonyl)-4,5-dihydro-1H-pyrazole-3-carbox-imidamide; 1-(4-chlorophenyl)-N-cyclohexyl-5-ethyl-2-(3-methylpyridin-2-yl)-1H-imidazole-4-carboxamide; 1-(4-chlorophenyl)-5-ethyl-2-(3-methylpyridin-2-yl)-N-piperidin-1-yl-1H-imidazole-4-carboxamide; 1-(4-chlorophenyl)-2-(2,4-dichlorophenyl)-5-methyl-N-[4-(tri-fluoromethyl)benzyl]-1H-imidazole-4-carboxamide; 2-(2,4-dichlorophenyl)-5-methyl-N-piperidin-1-yl-1-pyridin-2-yl-1H-imidazole-4-carboxamide; 1-(4-bromophenyl)-2-(2,4-di-chlorophenyl)-5-ethyl-N-piperidin-1-yl-1H-imidazole-4-carboxamide; 1-(2,4-dichloro-phenyl)-N-methyl-N'-(morpholin-4-ylsulfonyl)-5-phenyl-4,5-dihydro-1H-pyrazole-3-carbox-imidamide; 1-(4-chlorophenyl)-2-(2,4-dichlorophenyl)-5-ethyl-N-piperidin-1-yl-1H-imidazole-4-carboxamide; 1-(4-chlorophenyl)-2-(2,4-dichlorophenyl)-5-(fluoromethyl)-N-piper-idin-1-yl-1H-imidazole-4-carboxamide; 1-(4-chlorophenyl)-2-(2,4-dichlorophenyl)-5-(hydroxylmethyl)-N-piperidin-1-yl-1H-imidazole-4-carboxamide; 3-(4-chlorophenyl)-N'-[(4-chlorophenyl)sulfonyl]-N-(2-fluoroethyl)-4-phenyl-4,5-dihydro-1H-pyrazole-1-carbox-imidamide; 1-(4-chlorophenyl)-N-cyclohexyl-2-(2,4-dichlorophenyl)-5-(methylthio)-1H-imidazole-4-carboxamide; 1-(4-chlorophenyl)-2-(2,4-dichlorophenyl)-5-(methylsulfonyl)-N-piperidin-1-yl-1H-imidazole-4-carboxamide; 1-(4-chlorophenyl)-2-(2,4-dichlorophenyl)-5-(methylsulfinyl)-N-piperidin-1-yl-1H-imidazole-4-carboxamide; 3-(4-chlorophenyl)-N-methyl-4-pyridin-3-yl-N'-{[4-(trifluoromethyl)phenyl]sulfonyl}-4,5-dihydro-1H-pyrazole-1-carboximidamide; 5-(4-chlorophenyl)-4-(2,5-dichlorophenyl)-1-methyl-N-piperidin-1-yl-1H-imidazole-2-carboxamide; 2-(2-chlorophenyl)-1-(5-chloropyridin-2-yl)-5-ethyl-N-piperidin-1-y-1H-imidazole-4-carboxamide; 1-(4-chlorophenyl)-2-(2,4-dichlorophenyl)-N-piperidin-1-yl-5-(2,2,2-trifluoroethyl)-1H-imidazole-4-carboxamide; 1-(5-chloropyridin-2-yl)-2-(2,4-dichlorophenyl)-5-ethyl-N-piperidin-1-yl-1H-imidazole-4-carboxamide; N-[1-(4-chloro-phenyl)-2-(2,4-dichlorophenyl)-5-methyl-1H-imidazol-4-yl]benzamide; 3-(4-chlorophenyl)-N'-[(dimethylamino)sulfonyl]-4-(3-fluorophenyl)-N-methyl-4,5-dihydro-1H-pyrazole-1-carboximidamide; 1-(4-chlorophenyl)-2-(2,4-dichlorophenyl)-N-piperidin-1-yl-5-(pyrrolidin-1-ylmethyl)-1H-imidazole-4-carboxamide; (4S)-3-(4-chlorophenyl)-N'-[(4-chloro-phenyl)-sulfonyl]-4-(3-fluorophenyl)-N-methoxy-4,5-dihydro-1H-pyrazole-1-carbox-imidamide; N-[5-(4-chlorophenyl)-1-(2,4-dichlorophenyl)-4-methyl-1H-pyrazol-3-yl]piperidine-1-carboxamide; 1-(4-bromophenyl)-5-chloro-2-(2,4-dichlorophenyl)-N-piperidin-1-yl-1H-imidazole-4-carboxamide; 2-[1-(4-chlorophenyl)-2-(2,4-dichlorophenyl)-5-methyl-1H-imidazol-4-yl]-hexan-2-ol; (4S)-3-(4-chlorophenyl)-N-methyl-4-phenyl-N'-(piperidin-1-ylsulf-onyl)-4,5-dihydro-1H-pyrazole-1-carboximidamide; N-1-adamantyl-5-pentyl-4-phenyl-1,3-thiazole-2-carboxamide; 1-(4-chlorophenyl)-2-(2,4-dichlorophenyl)-N-piperidin-1-yl-1H-imidazole-4-carboxamide; N-1-adamantyl-4-pentyl-5-phenyl-1,3-thiazole-2-carboxamide; 1-(4-chlorophenyl)-2-(2,4-dichlorophenyl)-5-methyl-4-pentyl-1H-imidazole; 3-(4-chloro-phenyl)-N'-[(4-chlorophenyl)sulfonyl]-4-phenyl-4,5-dihydro-1H-pyrazole-1-carbox-imidamide; 1-(4-chlorophenyl)-2-(2,4-dichlorophenyl)-5-(ethylthio)-N-piperidin-1-yl-1H-imidazole-4-carboxamide; (4S)-3-(4-chlorophenyl)-N'-[(4-chlorophenyl)sulfonyl]-4-phenyl-4,5-dihydro-1H-pyrazole-1-carboximidamide; and mixtures thereof.

The above mentioned compounds and their synthesis have been published in e.g., U.S. 2005-0171179-A1 (published Aug. 04, 2005) and U.S. 2005-0187259-A1 (published Aug. 25, 2005).

Dependent on the exact activity profiles of a specific active agent or a combination of active agents according to the invention, a combination of a dually acting compound, said compound comprising combined $K_{ATP}$ channel opening and $CB_1$ antagonistic properties with a $CB_1$ antagonist and/or a $K_{ATP}$ channel opener may also be suitable. Dually acting compounds, said compounds comprising combined $K_{ATP}$ channel opening and $CB_1$ antagonistic properties, may also be used as the first active agent a) according to the invention. Dually acting compounds, said compound comprising combined $K_{ATP}$ channel opening and $CB_1$ antagonistic properties, may also be used as the second active agent b) according to the invention.

In a second aspect, the invention pertains to a use of at least one $K_{ATP}$ channel opener in combination with at least one $CB_1$ antagonist for the manufacture of a medicament for the prophylaxis, treatment and/or inhibition of obesity.

In a specific and preferred embodiment of said second aspect of the invention, a dually acting compound, said compound comprising combined $K_{ATP}$ channel opening and $CB_1$ antagonistic properties, may be used.

In a third aspect, the invention pertains to a use of at least one $K_{ATP}$ channel opener in combination with at least one $CB_1$ antagonist for the manufacture of a medicament for the prophylaxis, treatment, delayed progression, delayed onset and/or inhibition of diabetes mellitus.

In a specific and preferred embodiment of said third aspect of the invention, insulin is added as a third component. It is within the scope of this third aspect of the invention, that the use of at least one $K_{ATP}$ channel opener in combination with at least one $CB_1$ antagonist, optionally with added insulin as a third component, is suitable for the weight-loss independent prophylaxis, treatment, delayed progression, delayed onset and/or inhibition of diabetes type I and/or diabetes type II.

In another specific and preferred embodiment of said third second aspect of the invention, a dually acting compound, said compound comprising combined $K_{ATP}$ channel opening and $CB_1$ antagonistic properties, may be used.

In a fourth aspect, the invention pertains to a use of at least one $K_{ATP}$ channel opener in combination with at least one $CB_1$ antagonist for the manufacture of a medicament for the prophylaxis or treatment of the metabolic syndrome and/or syndrome X in mammals and humans. The metabolic syndrome and/or syndrome X in this regard comprise in particular disorders or diseases chosen from hypertension, in particular arterial hypertension; insulin resistance, in particular type II diabetes; glucose intolerance; dyslipoproteinaemia, in particular as hypertriglyceridaemia accompanied by dyslipoproteinaemia occurring with lowered HDL-cholesterol and hyperuricaemia. Type II diabetes can be treated in mammals and humans with or without concomitant obesity. The medicament can preferably be a physical combination (fixed combination) of at least one $K_{ATP}$ channel opener and at least one $CB_1$ antagonist. In a specific and preferred embodiment of said fourth aspect of the invention, a dually acting compound, said compound comprising combined $K_{ATP}$ channel opening and $CB_1$ antagonistic properties, may be used.

In a fifth aspect, the invention pertains to a method of treating, preventing and/or inhibiting obesity, syndrome X and/or the metabolic syndrome in mammals and humans comprising administering to a subject in need thereof an effective amount of at least one $K_{ATP}$ channel opener in combination with at least one $CB_1$ antagonist.

In a specific and preferred embodiment of said fifth aspect, subjects with established obesity are treated to delay or prevent onset or aggravation of syndrome X and/or the metabolic syndrome. Type II diabetes and/or insulin resistance are the diseases or conditions which can most favorably be influenced in this regard.

In another specific embodiment of said fifth aspect of the invention, subjects with insulin resistance and type II diabetes without concomitant obesity can be treated.

When treating subjects with established type II diabetes with or without concomitant obesity, it is favourable to provide for insulin substitution for at least a certain period of time after starting therapy.

In a specific and preferred embodiment of said fifth aspect of the invention, a dually acting compound, said compound comprising combined $K_{ATP}$ channel opening and $CB_1$ antagonistic properties, may be used.

The at least one $K_{ATP}$ channel opener and the at least one $CB_1$ antagonist may be administered simultaneously, stepwise (separately) or in physical combination. A physical combination (fixed combination) is preferred.

In a sixth aspect, the invention pertains to a method of treating, delaying progression of, delaying onset of, and/or inhibiting diabetes mellitus in subjects comprising administering to a subject in need thereof an effective amount of at least one $K_{ATP}$ channel opener in combination with at least one $CB_1$ antagonist.

In a specific and preferred embodiment of said sixth aspect, insulin is added as a third component.

It is within the scope of this sixth aspect of the invention, that obese and non-obese subjects with diabetes type I and/or diabetes type II are treated weight-loss independently.

In a specific and preferred embodiment of said sixth aspect of the invention, a dually acting compound, said compound comprising combined $K_{ATP}$ channel opening and $CB_1$ antagonistic properties, may be used.

The at least one $K_{ATP}$ channel opener and the at least one $CB_1$ antagonist may be administered simultaneously, stepwise (separately) or in physical combination. A physical combination (fixed combination) is preferred.

In a seventh aspect, the invention pertains to a kit, comprising in separate containers in a single package pharmaceutical dosage forms for use in combination, comprising,
  i) in one separate container a pharmaceutical dosage form comprising at least one $K_{ATP}$ channel opener, and
  ii) in a second separate container a pharmaceutical dosage form comprising at least one $CB_1$ antagonist.

In particular, the kit may comprise at least one $CB_1$ antagonistic compound, preferably the $CB_1$ antagonistic compound having formula I as defined above, or a prodrug, tautomer or salt thereof, in combination with at least one $K_{ATP}$ channel opener, suitable for simultaneous, separate or step-wise administration. Further, such kit may also comprise a leaflet indicating that the at least one $CB_1$ antagonist may be administered in combination with at least one $K_{ATP}$ channel opener simultaneously, stepwise (separately) or in physical combination.

Thus, in one embodiment the active agents can be obtained and administered separately and can be incorporated in two or more separate unit dosage forms, e.g. in two or more tablets or capsules, the tablets or capsules being physically segregated from each other. In another embodiment, the active agents can be obtained separately, but administered in one single dosage form, e.g. in one tablet or capsule, wherein the different active agents are segregated from each other e.g. by means of different compartments in such capsule or different layers of such tablet, the segregation being in the latter case e.g. achieved by the use of inert intermediate layers.

In a preferred embodiment of this seventh aspect, the invention pertains to a kit comprising in a single container at least one pharmaceutical dosage form, said pharmaceutical dosage form is for use in combination, and comprises a dually acting compound having combined $K_{ATP}$ channel opening and $CB_1$ antagonistic properties.

In an eighth aspect, the invention pertains to a screening method for isolating compounds with combined $K_{ATP}$ channel opening and $CB_1$ antagonistic properties, comprising testing candidate compounds in parallel or in either order in a test model suitable for identifying compounds with $K_{ATP}$ channel opening activity and in a test model suitable for identifying compounds with $CB_1$ antagonistic properties and selecting compounds which are found to be active in both test models. This method allows one to screen for i.a. $CB_1$ antagonists that have especial efficacy for prophylaxis against development of syndrome X, metabolic syndrome or type II diabetes, or alternatively for $K_{ATP}$ channel openers that are also suitable for treatment of and prophylaxis against obesity. Suitable test methods for identifying compounds with $CB_1$ antagonistic properties are known in the art and comprise e.g. the test methods as set forth in this application. Suitable test methods for identifying compounds with $K_{ATP}$ channel opening properties are known in the art and comprise e.g. the test methods as set forth in this application. The test methods for identifying compounds with $CB_1$ antagonistic properties and for identifying compounds with $K_{ATP}$ channel opening properties can be carried out in a manner known per se, usually sequentially and in either order.

In a ninth aspect, the invention pertains to a method for treating, preventing and/or inhibiting obesity, syndrome X and/or the metabolic syndrome and/or diabetes mellitus in mammals and humans, comprising identifying a compound which exhibits combined $K_{ATP}$ channel opening and $CB_1$ antagonistic properties, and administering a combined amount effective to treat or inhibit obesity, syndrome X and/or the metabolic syndrome and/or diabetes mellitus of said compound to said mammal or human.

Description of the Pharmacological Test Methods
1. In Vitro Binding Affinity of the Test Compounds to Rodent $K_{ATP}$ Channels Competitive binding experiments were performed to characterize the affinity of the test compounds for the binding sites for sulfonylureas and $K_{ATP}$ channel openers (=KCOs) on hamster SUR1. To assess the affinity for the sulfonylurea site membranes from COS-cells transiently expressing hamster SUR1 were incubated in the presence of [$^3$H]glibenclamide with increasing concentrations of test compounds. The affinity for binding to the KCO site was assessed by incubations in the additional presence of 100 µM MgATP (see Schwanstecher M., et al. Naunyn-Schmiedeberg's Arch. Pharmacol. 343 (1991) 83-89 and Schwanstecher M. et al., EMBO J. 17 (1998) 5529-5535 (=Schwanstecher et al., 1998)). For each test compound 4 displacement curves were measured (±MgATP from the human and hamster isoform). Per curve 9-15 distinct concentrations were tested covering the relevant range. All measurements were repeated at least 5 times in independent experiments.

Similar to SUR1 (see above) competitive binding experiments were performed to characterize the affinity of the test compounds for the binding sites for sulfonylureas and KCOs on rat SUR2A. The affinity for the KCO site on SUR2A was assessed by displacement of [$^3$H]P1075 (see Schwanstecher et al., 1998; Dörschner H. et al. Mol. Pharmacol. 55 (1999) 1060-1066 (=Dörschner et al., 1999)). The affinity of [$^3$H] glibenclamide for the human SUR2 isoforms, however, is too weak to allow direct detection of binding using filtration assays. Therefore, two strategies can be used to detect binding to the sulfonylurea site on SUR2A. First, binding can be detected indirectly through allosteric displacement of [$^3$H] P1075 (Dörschner et al., 1999). Second, a mutated SUR2A (SUR2A$_{Y1205S}$, see above) with increased affinity for [$^3$H] glibenclamide allowing direct displacement of this tracer can be used. This second approach was chosen to enable discrimination between allosteric and competitive interaction with the KCO site and make sure that binding of ligands which do not induce allosteric displacement are not missed.

Membranes from COS-cells transiently expressing rat SUR2A were incubated in the presence of the radioligands with increasing concentrations of test compounds as described above. The affinity for binding to the KCO site was assessed by incubations in the additional presence of 100 µM MgATP (Schwanstecher et al., 1991 and 1998). For each test compound 4 displacement curves were measured (displacement of [$^3$H]P1075 from the rat isoform of the wild type receptor and displacement of [$^3$H]glibenclamide from the rat isoform of SUR2A$_{Y1205S}$). Per curve 9-15 distinct concentrations were tested covering the relevant range. All measurements were repeated at least 5 times in independent experiments.

[$^3$H]P1075 (specific activity 116 Ci mmol$^{-1}$) was purchased from Amersham Buchler (Braunschweig, Germany). [$^3$H]glibenclamide (specific activity 51 Ci mmol$^{-1}$) was obtained from NEN (Dreieich, Germany). If suitable, stock solutions were prepared in dimethylsulfoxide with a final solvent concentration in the media below 1%.

SUR- or Kir6.x isoforms were used either subcloned in the pcDNA (hamster SUR1, mouse Kir6.2) or pCMV vector (rat SUR2A, SUR2B).

Rodent SUR-isoforms and $K_{ATP}$ channels were transiently expressed in COS-1 cells as described (see Schwanstecher et al., 1998); Dörschner et al., 1999); Uhde I. et al. J Biol Chem 274 (1999) 28079-28082; Gross I. et al. Mol. Pharmacol. 56 (1999) 1370-1373; Markworth E., Diabetes 49 (2000) 1413-1418). A mutated form of the SUR2 isoforms with the phenylalanine residue in position 1205 substituted with a serine (SUR2$_{Y1205S}$) was used to allow detection of binding to the sulfonylurea site of these isoforms by displacement of [$^3$H] glibenclamide (Uhde I., Dissertation 2001). Briefly, COS-1 cells cultured in DMEM HG (10 mM glucose), supplemented with 10% fetal calf serum (FCS), were plated at a density of 5×10$^5$ cells per dish (94 mm) and allowed to attach overnight.

For transfection the cells were incubated 4 hours in a Tris-buffered salt solution containing DNA (5-10 µg/ml) plus DEAE-dextran (1 mg/ml), 2 min in HEPES-buffered salt solution plus dimethylsulfoxide (10%) and 4 hours in DMEM-HG plus chloroquine (100 µM). Cells were then returned to DMEM-HG plus 10% FCS. Membranes were prepared 60-72 h post transfection as described (Schwanstecher M. et al., Br. J. Pharmacol. 106 (1992) 295-301 (=Schwanstecher et al., 1992)). For binding experiments resuspended membranes (final protein concentration 5-50 µg/ml) were incubated in "Tris-buffer" (50 mM, pH 7.4) containing either [$^3$H]glibenclamide (final concentration 0.3 nM or 3 nM and nonspecific binding defined by 100 nM or 1 µM glibenclamide for SUR1 or $SUR2_{Y1205S}$-isoforms, respectively) or [$^3$H]P1075 (final concentration 3 nM, nonspecific binding defined by 100 µM pinacidil) and increasing concentrations of the test compounds. The free $Mg^{2+}$ concentration were kept close to 0.7 mM. ATP (0.1 mM) was added to incubation media to enable KCO (e.g. diazoxide, [$^3$H] P1075) binding (see Schwanstecher et al., 1998). Incubations were carried out for 1 h at room temperature and were terminated by rapid filtration through Whatman GF/B filters.

The inhibition constant (Ki value) of the test substances was calculated from the respective $IC_{50}$ value, and was stated as the negative logarithmised value thereof ($pK_i$).

The binding affinity and selectivity of a given compound towards SUR1 and SUR2 can be used as criteria to reflect the modulation of the K-ATP channel (e.g. NN-414, with a pKi 6.2, is 100 times more potent than diazoxide, with a pKi 3.8, to inhibit glucose-stimulated insulin release). The binding data can be used as first estimate of the potential of a given compound to preserve beta cell function and to prevent or delay the progression of diabetes.

In this test model the test substances listed in claim 16 showed the $pk_i$ values on rat SUR1 between 4.0 and 7.0. In this test model the test substances listed in claim 16 showed the $pk_i$ values on rat SUR2 between 4.0 and 6.3.

Compound having a pki (SUR1) larger than pki (SUR2) are particularly preferred for the purposes of the present invention. This is specifically true for (4S)-3-(4-chlorophenyl)-N'-[(4-chlorophenyl)sulfonyl]-N-methyl-4-phenyl-4,5-dihydro-1H-pyrazole-1-carboximid-amide; 5-(1,1-dimethylheptyl)-2-[(1R,2R,5R)-5-hydroxy-2-(3-hydroxypropyl)cyclohexyl]-phenol; (2S)-1-[3-(4-chlorophenyl)-4-phenyl-4,5-dihydro-1H-pyrazol-1-yl]-3-(3,4-dichloro-phenyl)-1-oxopropan-2-amine; 3-(4-chlorophenyl)-N'-[(4-chlorophenyl)sulfonyl]-4-phenyl-N-(pyridin-3-ylmethyl)-4,5-dihydro-1H-pyrazole-1-carboximidamide; (2S)-1-[3-(4-chloro-phenyl)-4-phenyl-4,5-dihydro-1H-pyrazol-1-yl]-3-(1H-indol-3-yl)-N-methyl-1-oxopropan-2-amine; 2-[3-(4-chlorophenyl)-4-phenyl-4,5-dihydro-1H-pyrazol-1-yl]-5-ethyl-4,5-dihydro-1,3-oxazole; 3-(4-chlorophenyl)-N'-[(4-chlorophenyl)sulfonyl]-N-[(1-methylpyrrolidin-3-yl)-methyl]-4-phenyl-4,5-dihydro-1H-pyrazole-1-carboximidamide; 5-(4-bromophenyl)-N-[(4-chlorophenyl)sulfonyl]-1-(2,4-dichlorophenyl)-1H-pyrazole-3-carboxamide; 8-chloro-1-(2,4-dichlorophenyl)-N-piperidin-1-yl-1,4,5,6-tetrahydrobenzo[6,7]cyclohepta[1,2-c]pyrazole-3-carboxamide; 1-[bis(4-chlorophenyl)methyl]-3-[(3,5-difluorophenyl)(methylsulfonyl)-methylene]azetidine; 2-{1-[bis(4-chlorophenyl)methyl]azetidin-3-yl}-1,2-benzisothiazol-3(2H)-one 1,1-dioxide; 1-(4-bromophenyl)-2-(2,4-dichlorophenyl)-5-ethyl-N-pentyl-1H-imidazole-4-carboxamide; 3-(4-chlorophenyl)-N'-[(dimethylamino)sulfonyl]-N-(2-fluoro-ethyl)-4-phenyl4,5-dihydro-1H-pyrazole-1-carboximidamide; 3-(4-chlorophenyl)-N-methyl-N'-(morpholin-4-ylsulfonyl)-4-phenyl-4,5-dihydro-1H-pyrazole-1-carboximidamide; 1-(4-chlorophenyl)-2-(2,4-dichlorophenyl)-N,N-diethyl-1H-imidazole-4-carboxamide; 3-(4-chlorophenyl)-N'-[(4-chlorophenyl)sulfonyl]-N-methyl-4-pyridin-3-yl-4,5-dihydro-1H-pyrazole-1-carboximidamide; 1-(4-chlorophenyl)-N-methyl-5-phenyl-N'-(piperidin-1-ylsulfonyl)-4,5-dihydro-1H-pyrazole-3-carboximidamide; 1-(4-bromophenyl)-2-(2,4-dichloro-phenyl)-5-ethyl-N-piperidin-1-yl-1H-imidazole-4-carboxamide; 1-(2,4-dichlorophenyl)-N-methyl-N'-(morpholin-4-ylsulfonyl)-5-phenyl-4,5-dihydro-1H-pyrazole-3-carboximidamide; 1-(4-chlorophenyl)-N-cyclohexyl-2-(2,4-dichlorophenyl)-5-(methylthio)-1H-imidazole-4-carboxamide; 3-(4-chlorophenyl)-N-methyl-4-pyridin-3-yl-N'-{[4-(trifluoromethyl)phenyl]-sulfonyl}-4,5-dihydro-1H-pyrazole-1-carboximidamide; N-[1-(4-chlorophenyl)-2-(2,4-di-chlorophenyl)-5-methyl-1H-imidazol-4-yl]benzamide; 3-(4-chlorophenyl)-N'-[(dimethyl-amino)sulfonyl]-4-(3-fluorophenyl)-N-methyl-4,5-dihydro-1H-pyrazole-1-carboximidamide; 2-[1-(4-chlorophenyl)-2-(2,4-dichlorophenyl)-5-methyl-1H-imidazol-4-yl]hexan-2-ol; 1-(4-chlorophenyl)-2-(2,4-dichlorophenyl)-5-methyl-4-pentyl-1H-imidazole; 3-(4-chlorophenyl)-N'-[(4-chlorophenyl) sulfonyl]-4-phenyl-4,5-dihydro-1H-pyrazole-1-carboximidamide; (4S)-3-(4-chlorophenyl)-N'-[(4-chlorophenyl)sulfonyl]-4-phenyl-4,5-dihydro-1H-pyrazole-1-carboximidamide;

and mixtures of any of the above compounds.

2. In Vitro Binding Affinity of the Test Compounds to Rodent $CB_1$ Receptors (Radioligand: Antagonist [$^3$H]-SR141716A)

The affinity of the compounds of the invention for cannabinoid $CB_1$ receptors can be determined using membrane preparations of Chinese hamster ovary (CHO) cells in which the human cannabinoid $CB_1$ receptor is stably transfected in conjunction with [$^3$H]-SR141716A as radioligand. After incubation of a freshly prepared cell membrane preparation with the [$^3$H]-ligand, with or without addition of compounds of the invention, separation of bound and free ligand is performed by filtration over glassfiber filters. Radioactivity on the filter is measured by liquid scintillation counting.

In this test model the test substances listed in claim 16 showed the $pk_i$ values on radio antagonist [$^3$H]-SR141716A between 6.9 and 9.4.

3. In Vitro Binding Affinity of the Test Compounds to Rodent $CB_1$ Receptors (Radioligand: Agonist CP-55.940)

The affinity of the compounds of the invention for cannabinoid $CB_1$ receptors can be determined using membrane preparations of Chinese hamster ovary (CHO) cells in which the human cannabinoid $CB_1$ receptor is stably transfected in conjunction with [$^3$H]CP-55,940 as radioligand. After incubation of a freshly prepared cell membrane preparation with the [$^3$H]-ligand, with or without addition of compounds of the invention, separation of bound and free ligand is performed by filtration over glassfiber filters. Radioactivity on the filter is measured by liquid scintillation counting.

In this test model the test substances listed in claim 16 showed the $pk_i$ values on radio agonist CP-55,940 between 6.0 and 8.6.

4. Functional Activity of the Test Compounds at Human Cannabinoid $CB_1$ Receptors In vitro $CB_1$ receptor antagonism can be assessed with the human $CB_1$ receptor cloned in CHO cells. CHO cells were grown in a Dulbecco's Modified Eagle's culture medium (=DMEM) and supplemented with 10% heat-inactivated fetal calf serum. The medium was aspirated and replaced by DMEM, without fetal calf serum, but containing [$^3$H]-arachidonic acid and incubated overnight in a cell culture stove (5% $CO_2$/95% air; 37° C.; water-saturated atmosphere). During this period [$^3$H]-arachidonic acid was incorporated in membrane phospholipids. On the test day, medium was aspirated and cells were washed three times using 0.5 mL DMEM, containing 0.2% bovine serum albumin (BSA). Stimulation of the $CB_1$ receptor by WIN 55,212-2 led to activation of $PLA_2$ followed by release of [$^3$H]-arachidonic acid into the medium. This WIN 55,212-2-induced release was concentration-dependently antagonized by $CB_1$ receptor antagonists. The $CB_1$ antagonistic potencies of the test compounds are expressed as $pA_2$ values.

The ligand displacement of a radio-labelled antagonist or agonist from the CB1 receptor by a given compound, and its functional effects on CB1-mediated arachidonic acid release can be used as criteria to reflect the modulation of the CB1 receptor. These in vitro data can be used as first estimate of the potential of a given compound to cause weight loss.

In this test model the test substances listed in claim 16 showed the $pA_2$ values between 7.2 and 9.9.

5. Determination of the Antagonist Effects of Compounds on Insulin Secretion in Rat Perifused Pancreatic Islets—Simple Screen for Antagonist Activity Animals: Male Wistar rats in the weight range 175-200 g were group housed in standard animal cages at a temperature of 21±2° C. and humidity of 55±10%. Animals were maintained on a 12 h light-dark cycle (lights on 06.00-18.00 h) with free access to standard rodent diet (B&K Universal Ltd standard rat and mouse diet (BK 001P), Beekay Feeds, B&K Universal Ltd, Hull, East Riding of Yorkshire) and tap water. The rats were accustomed to these conditions for at least one week before experimentation.

Experimental procedures: After the rats were sacrificed, the branch of the bile duct leading to the liver and the duodenal end of the duct in the pancreas were clamped and the pancreas distended by injection of ice-cold 0.9 mg/ml collagenase solution into the bile duct. The pancreas were then removed and incubated statically for 10-12 min at 37° C. Following the incubation, 10 ml of cold buffer was added and the suspension shaken vigorously by hand for 1 min. The islets were allowed to settle for 5 min on ice and washed three times using ice-cold buffer. Well formed and good sized islets from 3 rats were hand-picked (under a low power microscope) and pooled and a final selection of islet transferred to the perifusion apparatus. Oxygenated (95% $O_2$/5% $CO_2$) Gey & Gey buffer containing 1 mg/ml bovine serum albumin and 4 mM glucose were used throughout the experiment unless otherwise stated (see Dickinson et al. Eur J Pharmacol 1997;339:69-76 for further details).

Compounds were either tested at an advised concentration or the solubility was determined in the experimental conditions and a maximum soluble drug concentration used for experiments (DMSO or ethanol will be used as the solvents at a maximum 0.1% in the assay buffer).

On each day, two experiments were performed in parallel in 2 identical, independent sets of perifusion apparatus each consisting of sufficient number of chambers. Each chamber was loaded with 20 hand-picked islets. Islets were perifused for an initial 30 min period in media containing 4 mM glucose. Perifusate was then collected at 2 min intervals for the remainder of the experiment. After the first 10 min of the experiment (to collect baseline insulin values), the media in each chamber was switched to one containing 11 mM glucose and the relevant drug concentration/vehicle/diazoxide concentration and perifusate collected for a further 62 min to produce a total of 36 fractions for each chamber.

Perifusate samples were then pooled to create 3 samples per chamber as follows: Baseline (4 mM): Samples 1-5 (first 10 minutes); 0-30 minutes (11 mM glucose): Samples 6-21; 30-60 minutes (11 mM glucose): Samples 22-36.

Experiment 1—Effect of Compounds on Insulin Secretion at 11 mM glucose

| Chamber | Glucose concentration mM | Treatment/dose |
| --- | --- | --- |
| 1 | 4 mM | Vehicle |
| 2 | 11 mM | Diazoxide |
| 3 | 11 mM | Vehicle |
| 4 | 11 mM | compound 1 |
| 5 | 11 mM | compound 2 |
| 6 | 11 mM | compound 3 |
| 7 | 11 mM | compound 4 |

Experiments 2 and 3 were exact repeats of experiment 1.

Perifusate fractions were stored at −75° C. until required for insulin assay. Insulin content of fractions were assayed using a 96-well ELISA assay (Mercodia). Initial insulin assays were performed in triplicate on three pooled fractions from each chamber (18 samples per experiment, 108 samples in total for 6 experiments).

Drugs: All chemicals will be obtained from Sigma (or other appropriate commercial supplier).

Result: The three islet preparations showed a consistent degree of glucose dependent insulin secretion. The mean insulin secretion at 11 mM glucose was 98.3±12.6 pg/islet/min and 130.4±22.0 pg/islet/min at 0-30 and 30-60 minutes, respectively. In the presence of 4 mM glucose this was significantly lower and was 3.8±0.6 pg/islet/min and 3.4±0.1 pg/islet/min at 0-30 and 30-60 minutes, respectively. Thus, insulin secretion was increased by 26 times and 38 times by 11 mM glucose at 0-30 and 30-60 minutes, respectively. Data were initially expressed as a simple mean of the 3 experiments for insulin secretion (pg/islet/min) and multiple t-tests (against the corresponding vehicle time period) used to determine potential significant effects of treatments. Alternatively, data were also calculated as a % vehicle effect for each experimental day. This latter approach was deemed to be the more powerful analysis as it corrected for the day to day variation in insulin release from the islets. Diazoxide significantly inhibited insulin secretion by an average of 55.3% (0-30 min) and 58.9% (30-60 min).

Compounds 3 and 4 significantly inhibited insulin secretion at both 0-30 and 30-60 min and by an amount that was notably greater than diazoxide at 30-60 min. Compounds 1 and 2 both significantly inhibited insulin secretion (only at 0-30 min for compound 2) though by an amount that was similar or slightly less than that of diazoxide.

This test provides proof that candidate compounds selected on the basis of their affinity for the K-ATP channel do inhibit glucose-stimulated insulin secretion.

6. Detailed Determination of the Antagonist Effects of Compounds on Insulin Secretion in Rat Perifused Pancreatic Islets—in Depth Investigation of Compound Activity Animals: Male Wistar rats in the weight range 175-200 g were group housed in standard animal cages at a temperature of 21±2° C. and humidity of 55±10%. Animals were maintained on a 12 h light-dark cycle (lights on 06.00-18.00 h) with free access to standard rodent diet (B&K Universal Ltd standard rat and mouse diet (BK 001 P), Beekay Feeds, B&K Universal Ltd, Hull, East Riding of Yorkshire) and tap water. The rats were accustomed to these conditions for at least one week before experimentation.

Experimental procedures: Three rats (sufficient for the isolation of enough islets to allow for 2 perifusion experiments per day) were sacrificed, the branch of the bile duct leading to the liver and the duodenal end of the duct in the pancreas were clamped and the pancreas distended by injection of ice-cold 0.9 mg/ml collagenase solution into the bile duct. The pancreas were then removed and incubated statically for 10-12 min at 37° C. Following the incubation, 10 ml of cold buffer was added and the suspension shaken vigorously by hand for 1 min. The islets were allowed to settle for 5 min on ice and washed three times using ice-cold buffer. Well formed and good sized islets from 3 rats were hand-picked (under a low power microscope) and pooled and a final selection of islet transferred to the perifusion apparatus. Oxygenated (95% $O_2$/5% $CO_2$) Gey & Gey buffer containing 1 mg/ml bovine serum albumin and 4 mM glucose were used throughout the experiment unless otherwise stated (see Dickinson et al. Eur J Pharmacol 1997;339:69-76 for further details).

On each day, two experiments were performed in parallel in 2 identical, independent sets of perifusion apparatus each consisting of sufficient number of chambers. Each chamber was loaded with 20 hand-picked islets. Islets were perifused for an initial 30 min period in media containing 4 mM glucose. Perifusate was collected at 2 min intervals for the remainder of the experiment. After the first 10 min of the experiment (to collect baseline insulin values), the media in each chamber were switched to one containing the relevant drug concentration/vehicle/glucose concentration and perifusate collected for a further 62 min to produce a total of 36 fractions for each chamber.

Experiments were organised to evaluate firstly (Phase I) the effect of Compounds at a single concentration on glucose-stimulated insulin secretion (two independent sets of experiments) and secondly (Phase II), determination of the dose-dependent effect of these compounds to inhibit insulin secretion at 11 mM glucose (three independent sets of experiments).

Phase 1: effect of compound A evaluated at a single concentration, on glucose-stimulated insulin release.

Day 1—experiment 1—effect of compound A on insulin secretion at varying glucose concentrations

| chamber | glucose concentration mM | treatment/dose |
| --- | --- | --- |
| 1 | 4 mM | vehicle |
| 2 | 4 mM | compound A |
| 3 | 8 mM | vehicle |
| 4 | 8 mM | compound A |
| 5 | 16 mM | vehicle |
| 6 | 16 mM | compound A |

Day 2—experiment 2—repeat of experiment 1

Phase 2: evaluation of the dose dependency of compound A on insulin secretion at a single glucose concentration Day 3—experiment 3—effect of compound A on insulin secretion at varying glucose concentrations

| chamber | glucose concentration mM | compound |
| --- | --- | --- |
| 1 | 11 mM | vehicle |
| 2 | 11 mM | compound A dose 1 |
| 3 | 11 mM | compound A dose 2 |
| 4 | 11 mM | compound A dose 3 |
| 5 | 11 mM | compound A dose 4 |
| 6 | 11 mM | Diazoxide |

Day 4—experiment 4, repeat of experiment 3; effect of compound A on insulin secretion e Day 5—experiment 5, repeat of experiment 4; effect of compound A on insulin secretion Perifusate fractions were stored at −75° C. until required for insulin assay. Insulin content of fractions were assayed using a 96-well ELISA assay (Mercodia). Initial insulin assays were performed on only every third fraction (72 assays per experiment).

Drugs: All chemicals will be obtained from Sigma (or other appropriate commercial supplier).

Results:

Glucose dependency of insulin secretion in rat pancreatic islets (Phase 1 and Phase 2): The glucose responsiveness of the islets was very consistent between experiments so data from both the Phase 1 and Phase 2 experiments were combined. The 6 perifusion experiments showed a glucose dependent insulin secretion consistent with previously published data (Dickinson et al 1997 Eur J Pharmacol; 339: 69-76). The determined EC50 value for glucose-stimulated insulin secretion of 10 mM is very close to that determined previously (11 mM) and mean insulin secretion increased by 41× when glucose increased from 4 mM to 16 mM.

Phase 1: Effect of compound A at 10 μM on glucose dependent insulin secretion in rat pancreatic islets: There was no effect of compound A on insulin secretion at 4 mM glucose in two experiments and a slight effect to stimulate insulin secretion in one experiment. Compound A completely inhibited insulin secretion at 8 mM glucose in two of the experiments and moderately inhibited insulin secretion in the third experiment. At 16 mM glucose, compound A produced a moderate effect to inhibit insulin secretion in one experiment but only a slight effect in the other experiment.

Phase 2: Dose dependent effect of compound A and diazoxide on time-dependent insulin secretion at 11 mM glucose in rat pancreatic islets: The vehicle (11 mM glucose) was associated with the expected increase in time-dependent insulin secretion. Diazoxide at 100 μM almost completely blocked the stimulatory effect of 11 mM glucose whilst diazoxide at 10 μM produced only a partial inhibition. Compound A produced dose-dependent effects to block insulin secretion. The highest (10 μM) dose of each compound was clearly more effective than the comparable (10 μM) dose of diazoxide.

Phase 2: Dose dependent effect of compound A and diazoxide on mean insulin secretion at 11 mM glucose in rat pancreatic islets: The vehicle (11 mM glucose) produced an average insulin secretion of 162.3±18.2 pg/islet/min. Diazoxide at both 10 μM and 100 μM significantly reduced insulin secretion in a dose dependent manner (50% and 94%, respectively). Compound A also produced dose-dependent effects to inhibit mean insulin secretion and this attained statistical significance for the two highest (3 μM and 10 μM) doses of each. The highest (10 μM) dose of compound A was clearly more effective than the comparable (10 μM) dose of diazoxide (74% inhibition, respectively).

The test confirms the lack of agonist effect and the potency of the candidate compounds to inhibit glucose-stimulated insulin release and thus their potential to preserve pancreatic beta cell function and to prevent or delay the progression of diabetes.

Compound 1: (2S)-1-[3-(4-chlorophenyl)-4-phenyl-4,5-dihydro-1H-pyrazol-1-yl]-3-(1H-indol-3-yl)-N-methyl-1-oxopropan-2-amine Compound 2: 3-(4-chlorophenyl)-N-[2-(dimethylamino)ethyl]-4-phenyl-N'-(piperidin-1-ylsulfonyl)-4,5-dihydro-1H-pyrazole-1-carboximidamide Compound 3: (4S)-3-(4-chlorophenyl)-N-methyl-4-phenyl-N'-(piperidin-1-ylsulfonyl)-4,5-dihydro-1H-pyrazole-1-carboximidamide Compound 4: 3-(4-chlorophenyl)-N-methyl-4-pyridin-3-yl-N'-{[4-(trifluoromethyl)phenyl]sulfonyl}-4,5-dihydro-1H-pyrazole-1-carboximidamide Compound A: (4S)-3-(4-chlorophenyl)-N'-[(4-chlorophenyl)sulfonyl]-N-methyl-4-phenyl-4,5-dihydro-1H-pyrazole-1-carboximidamide 7. Influence of Chronic Drug Administration (4 Weeks) on Plasma Insulin and Glucose and on Oral Glucose Tolerance Test in Male Sugar Rats The studies were carried out in individually housed male fa/fa sugar rats weighing initially about 250 g. The rats were kept on a normal 12/12 h light/dark cycle (lights on 07.00) and they were allowed food (lab chow) and water ad libitum except for during experiments, when they were fasted overnight before the glucose challenge.

Test substance was suspended in 2% PEG in 1% carboxymethylcellulose and administered daily by oral gavage at a dose of 10 mg/kg/day; (1 ml/kg, 10 mg/ml) at 08.30-09.30 h for 4 weeks. Two groups of control animals received only the vehicle; one had free access to feed (except for the day preceding a blood sample), a second group of control animals was pair-fed to the test group.

On the day of the oral glucose tolerance test (OGTT), 45 min after the final dose of test substance/vehicle a blood sample (0 min) was taken (tail vein) immediately after which the rats received an oral glucose challenge (1.25 g/kg; 118 mg/ml). Further blood samples were taken at 30, 60, 90, 120 min after the glucose challenge.

The $2^{nd}$ drop of blood of each sample was placed on a glucose test strip before this was placed in the glucose meter for determination of blood glucose level (Life Scan One Touch Ultra Blood Glucose Meter and Life Scan One Touch Ultra Test Strips; Life Scan Inc.; Milpitas, Calif. 95035). The remaining blood of each sample was spun and the plasma was frozen at −80° C. before analysis for insulin (1-2-3 Rat Insulin ELISA kit, Alpco Diagnostics).

The values obtained were plotted and the AUC for test compounds and vehicle (for glucose and insulin) were determined after which the percent control AUC, percent control maximum value and % control baseline were estimated, to determine the influence of the test compound on the glucose tolerance.

On day 0, prior to administration of test compound, and on day 15, blood samples were taken in fasted rats without a subsequent glucose challenge; an OGTT was performed on day 29.

This test demonstrated the in vivo efficacy of a candidate compound and that its chronic oral administration caused beta cell rest (inhibition) which improved glycemic control (glycemic control at lower insulin levels) i.e. improved insulin sensitivity and delayed onset of diabetes.

8. Influence of 2 Week Chronic Drug Administration on Body Weight Gain in Male Sugar Rats Studies were performed in male sugar rats [[Ico: ZUCKER-fa/fa (fatty) (Orl] (Charles River France) weighing initially 400 to 490 g. Animals were housed two or three in a plastic cage in a temperature (20-24° C.), relative humidity (45-65%) and 12-h light/dark cycle (light 7:00 a.m. to 7:00 p.m.)—controlled room for 6 days before being used. All animals had free access to filtered tap water and standard pelleted laboratory chow (U.A.R., Villemois-son-sur-Orge, France). Animals were individually identified on the tail.

Experimental Protocol

At the end of the acclimatization period, animals were individually housed in wire-topped plastic cages. A pre-weighed quantity of food and water were placed on the roof grids. Each rat was acclimated to the handling and dosing procedure the 3 days preceding the start of treatment. Water and food intake was measured during the 24 h that followed dosing procedure to establish baseline food and water intake for each animal. Thereafter, the rats were randomly assigned to either vehicle or drug treatment groups.

Between 9:00-10:00 a.m. on the day of study, the animals were injected p.o. with either vehicle or differing doses of test compounds in a volume of 2 ml/kg each day for 14 consecutive days. During the 5-day post-treatment period, vehicle was given to all groups.

Daily food and water intake was determined per cage throughout the 14-day treatment period and the 5-day post-treatment period. Individual body weights were checked daily for the subsequent treatment and post-treatment periods. Data were collected before each dosing procedure.

(4S)-3-(4-chlorophenyl)-N'-[(4-chlorophenyl)sulfonyl]-N-methyl-4-phenyl-4,5-dihydro-1H-pyrazole-1-carboximidamide (3, 10 and 30 mg/kg p.o.) produced a sustained non dose-dependent reduction in body weight at all doses administered, the greatest reduction occuring with 10 mg/kg p.o. At the end of the treatment period (day 14), body weight was decreased by 5.3, 6.7 and 5.9% after (4S)-3-(4-chlorophenyl)-N'-[(4-chlorophenyl)sulfonyl]-N-methyl-4-phenyl-4,5-dihydro-1H-pyrazole-1-carboximidamide (3, 10 and 30 mg/kg p.o.) treatment respectively, in comparison to vehicle-treated rats. On interruption of drug treatment, body weight progressively returned towards control levels.

The pharmaceutical compositions according to the invention can be prepared in a manner known per se and thus can be obtained as formulations suitable for enteral, such as oral or rectal, administration or parenteral, such as injectable or transdermal, administration to mammals or humans, comprising a therapeutical effective amount of the pharmacologically active agents, alone or in combination with one or more pharmaceutically acceptable auxiliaries and/or carriers, especially suitable for enteral or parenteral application. Pharmaceutical compositions for enteral or parenteral administration, in particular those formulated for oral administration, are preferred and comprise for example unit dosage forms, such as coated tablets, tablets, capsules or suppositories and also ampoules. These are prepared in a manner which is known per se, for example using conventional mixing, granulation, coating, solubilizing or lyophilizing processes. Typical oral formulations include coated tablets, tablets, capsules, syrups, elixirs and suspensions. Capsules may contain the active agents e.g. in form of powders, granules, pellets, beadlets or microtablets. For example, a pharmaceutical composition according to the invention may consist of from about 0.1% to 90%, preferably of from about 1% to about 80%, of the active agents, the rest being made up by pharmaceutically acceptable auxiliaries and/or carriers. Thus, pharmaceutical compositions for oral use can be obtained by combining the active compounds with solid excipients, if desired granulating a mixture which has been obtained, and, if required or necessary, processing the mixture or granulate into tablets or coated tablet cores after having added suitable auxiliary substances. Typical injectable formulations include solutions and suspensions. Typical transdermal administration forms comprise e.g. patches, gels, ointments and the like.

The typical pharmaceutically acceptable auxiliaries and/or carriers for use in the formulations described above are exemplified by: sugars such as lactose, sucrose, mannitol and sorbitol; starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate and calcium stearate; stearic acid; vegetable oils such as peanut oil, cottonseed oil, sesame oil, olive oil and corn oil; non-ionic, cationic and anionic surfactants; ethylene glycol polymers; betacyclodextrin; fatty alcohols; and hydrolyzed cereal solids, as well as other non-toxic compatible fillers, binders, disintegrants, agents, e.g. talcum; buffers, preservatives, antioxidants, lubricants, flavoring and the like commonly used in pharmaceutical formulations.

EXAMPLE I

Capsules Containing 5-(4-chlorophenyl)-4-(2,4-dichlorophenyl)-N-(1-piperidinyl)-thiazole-2-carboxamide:

Capsules with the following composition per capsule were produced:

5-(4-Chlorophenyl)-4-(2,4-dichlorophenyl)-N-(1-piperidinyl)-thiazole-2-carboxamide 50 mg Corn starch 150 mg
Lactose 150 mg
Ethyl acetate q.s.

The active agents, the corn starch and the lactose were processed into a homogeneous pasty mixture using ethyl acetate. The paste was ground and the resulting granules were placed on a suitable tray and dried at 45° C. in order to remove the solvent. The dried granules were passed through a crusher and mixed in a mixer with the further following auxiliaries:
Talcum 15 mg
Magnesium stearate 15 mg
Corn starch 20 mg
and then poured into 400 mg capsules (=capsule size 0).

EXAMPLE II

Capsules Containing (4S)-3-(4-chlorophenyl)-N'-[(4-chlorophenyl)sulfonyl]-N-methyl-4-phenyl-4,5-dihydro-1H-pyrazole-1-carboximidamide Capsules with the following composition per capsule were produced:

(4S)-3-(4-chlorophenyl)-N'-[(4-chlorophenyl)sulfonyl]-N-methyl-4-phenyl-4,5-dihydro-1H-pyrazole-1-carboximidamide 50 mg Corn starch 150 mg
Lactose 150 mg
Ethyl acetate q.s.
The active agents, the corn starch and the lactose were processed into a homogeneous pasty mixture using ethyl acetate. The paste was ground and the resulting granules were placed on a suitable tray and dried at 45° C. in order to remove the solvent. The dried granules were passed through a crusher and mixed in a mixer with the further following auxiliaries:
Talcum 15 mg
Magnesium stearate 15 mg
Corn starch 20 mg
and then poured into 400 mg capsules (=capsule size 0).

EXAMPLE III

Capsules Containing (2S)-1-[3-(4-chlorophenyl)-4-phenyl-4,5-dihydro-1H-pyrazol-1-yl]-3-(1H-indol-3-yl)-N-methyl-1-oxopropan-2-amine Capsules with the following composition per capsule were produced:

(2S)-1-[3-(4-chlorophenyl)-4-phenyl-4,5-dihydro-1H-pyrazol-1-yl]-3-(1H-3-yl)-N-methyl-1-oxopropan-2-amine 50 mg Corn starch 150 mg
Lactose 150 mg
Ethyl acetate q.s.
The active agents, the corn starch and the lactose were processed into a homogeneous pasty mixture using ethyl acetate. The paste was ground and the resulting granules were placed on a suitable tray and dried at 45° C. in order to remove the solvent. The dried granules were passed through a crusher and mixed in a mixer with the further following auxiliaries:
Talcum 15 mg
Magnesium stearate 15 mg
Corn starch 20 mg
and then poured into 400 mg capsules (=capsule size 0).

EXAMPLE IV

Capsules Containing (4S)-3-(4-chlorophenyl)-N-methyl-4-phenyl-N'-(piperidin-1-ylsulfonyl)-4,5-dihydro-1H-pyrazole-1-carboximidamide Capsules with the following composition per capsule were produced:

(4S)-3-(4-chlorophenyl)-N-methyl-4-phenyl-N'-(piperidin-1-ylsulfonyl)-4,5-dihydro-1H-pyrazole-1-carboximidamide 50 mg Corn starch 150 mg
Lactose 150 mg
Ethyl acetate q.s.
The active agents, the corn starch and the lactose were processed into a homogeneous pasty mixture using ethyl acetate. The paste was ground and the resulting granules were placed on a suitable tray and dried at 45° C. in order to remove the solvent. The dried granules were passed through a crusher and mixed in a mixer with the further following auxiliaries:
Talcum 15 mg
Magnesium stearate 15 mg
Corn starch 20 mg
and then poured into 400 mg capsules (=capsule size 0).

EXAMPLE V

Capsules Containing (4S)-3-(4-chlorophenyl)-N-methyl-4-phenyl-N'-(piperidin-1-ylsulfonyl)-4,5-dihydro-1H-pyrazole-1-carboximidamide Capsules with the following composition per capsule were produced:

(4S)-3-(4-chlorophenyl)-N-methyl-4-phenyl-N'-(piperidin-1-ylsulfonyl)-4,5-dihydro-1H-pyrazole-1-carboximidamide 50 mg Corn starch 150 mg
Lactose 150 mg
Ethyl acetate q.s.

The active agents, the corn starch and the lactose were processed into a homogeneous pasty mixture using ethyl acetate. The paste was ground and the resulting granules were placed on a suitable tray and dried at 45° C. in order to remove the solvent. The dried granules were passed through a crusher and mixed in a mixer with the further following auxiliaries:

Talcum 15 mg
Magnesium stearate 15 mg
Corn starch 20 mg and then poured into 400 mg capsules (=capsule size 0).

EXAMPLE VI

Capsules Containing 3-(4-chlorophenyl)-N-methyl-4-pyridin-3-yl-N'-{[4-(trifluoromethyl)phenyl]sulfonyl}-4,5-dihydro-1H-pyrazole-1-carboximidamide Capsules with the following composition per capsule were produced:

3-(4-chlorophenyl)-N-methyl-4-pyridin-3-yl-N'-{[4-(trifluoromethyl)phenyl]sulfonyl}-4,5-dihydro-1H-pyrazole-1-carboximidamide 50 mg Corn starch 150 mg
Lactose 150 mg
Ethyl acetate q.s.

The active agents, the corn starch and the lactose were processed into a homogeneous pasty mixture using ethyl acetate. The paste was ground and the resulting granules were placed on a suitable tray and dried at 45° C. in order to remove the solvent. The dried granules were passed through a crusher and mixed in a mixer with the further following auxiliaries:

Talcum 15 mg
Magnesium stearate 15 mg
Corn starch 20 mg and then poured into 400 mg capsules (=capsule size 0).

We claim:

1. A method for treating type II diabetes and/or insulin resistance in a mammal or a human subject comprising:
    administering to a subject in need thereof an effective amount of at least one $K_{ATP}$ channel opener in combination with at least one $CB_1$ antagonist
    wherein the at least one $K_{ATP}$ channel opener is chosen from pinacidil; cromakalim; diazoxide; BPDZ 44; BPDZ 49; BPDZ 62; BPDZ 73; BPDZ 79; BPDZ 83; BPDZ 154; BPDZ 216 (=NNC 55-9216); NN414; NNC 55-0118; NNC 55-0462; MCC-134; SR 47063 and WAY 135201;

and wherein the at least one $CB_1$ antagonist is chosen from compounds of Formula I,

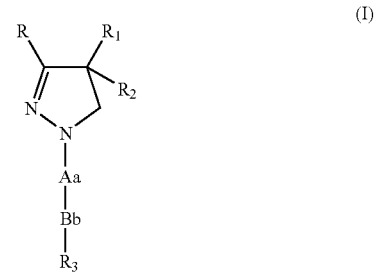

wherein:
R and $R_1$ are the same or different and are chosen from naphthyl, phenyl, thienyl and pyridyl groups, wherein the phenyl, thienyl and pyridyl groups may be substituted with 1, 2 or 3 substituents Y, which can each be the same or different;
$R_2$ is chosen from hydrogen, hydroxy, $C_{1-3}$-alkoxy, acetyloxy and propionyloxy groups;
Y is chosen from $C_{1-3}$-alkyl, $C_{1-3}$-alkoxy, hydroxy, halogen, trifluoromethyl, trifluoromethylthio, trifluoromethoxy, nitro, amino, mono- or dialkyl($C_{1-2}$)-amino, mono- or dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl groups;
Aa is chosen from one of the groups (i), (ii), (iii), (iv) and (v),

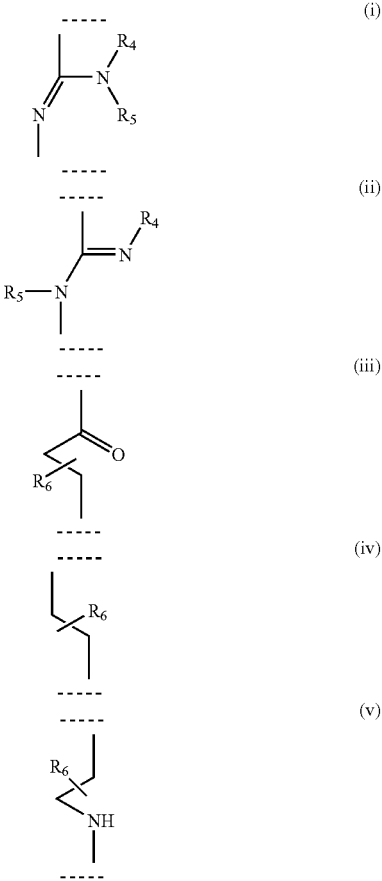

wherein
R$_4$ is chosen from acetamido, dimethylamino, 2,2,2-trifluoroethyl, phenyl, and pyridyl groups; and
R$_5$ is hydrogen; or
R$_4$ and R$_5$ independently of each other are chosen from hydrogen, C$_{1-8}$ branched or unbranched alkyl, and C$_{3-8}$ cycloalkyl groups;
R$_6$ is chosen from hydrogen and C$_{1-3}$ unbranched alkyl groups;
Bb is chosen from sulfonyl and carbonyl groups;
R$_3$ is chosen from pyrrolidinyl, piperidinyl, morpholinyl, naphthyl, benzyl, phenyl, thienyl and pyridyl groups, wherein the benzyl, phenyl, thienyl and pyridyl groups may be substituted with 1, 2 or 3 substituents Y, which can be the same or different;
a prodrug thereof, a tautomer thereof or a pharmaceutically acceptable salt thereof.

2. The method according to claim 1, wherein a subject without concomitant obesity is treated.

3. The method according to claim 1, further comprising administering to the subject insulin substitution as needed.

4. The method according to claim 1, wherein the at least one K$_{ATP}$ channel opener and the at least one CB$_1$ antagonist are administered simultaneously, stepwise, or in physical combination.

5. The method according to claim 1, wherein the at least one K$_{ATP}$ channel opener and the at least one CB$_1$ antagonist are administered simultaneously in a fixed combination.

6. The method according to claim 1, wherein the at least one CB$_1$ antagonist or the at least one K$_{ATP}$ channel opener is a dually acting compound comprising combined K$_{ATP}$ channel opening and CB$_1$ antagonistic properties.

7. A method for treating, delaying progression of, or delaying onset of diabetes mellitus in a subject comprising:
administering to a subject in need thereof an effective amount of at least one K$_{ATP}$ channel opener in combination with at least one CB$_1$ antagonist
wherein the at least one K$_{ATP}$ channel opener is chosen from pinacidil; cromakalim; diazoxide; BPDZ 44; BPDZ 49; BPDZ 62; BPDZ 73; BPDZ 79; BPDZ 83; BPDZ 154; BPDZ 216 (=NNC 55-9216); NN414; NNC 55-0118; NNC 55-0462; MCC-134; SR 47063 and WAY 135201;
and wherein the at least one CB$_1$ antagonist is chosen from compounds of Formula I,

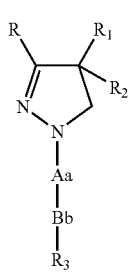

(I)

wherein:
R and R$_1$ are the same or different and are chosen from naphthyl, phenyl, thienyl and pyridyl groups, wherein the phenyl, thienyl and pyridyl groups may be substituted with 1, 2 or 3 substituents Y, which can each be the same or different;
R$_2$ is chosen from hydrogen, hydroxy, C$_{1-3}$-alkoxy, acetyloxy and propionyloxy groups;

Y is chosen from C$_{1-3}$-alkyl, C$_{1-3}$-alkoxy, hydroxy, halogen, trifluoromethyl, trifluoromethylthio, trifluoromethoxy, nitro, amino, mono- or dialkyl (C$_{1-2}$)-amino, mono-or dialkyl (C$_{1-2}$)-amido, (C$_{1-3}$)-alkyl sulfonyl, dimethylsulfamido, C$_{1-3}$-alkoxycarbonyl, carboxyl, trifluoromethylsulfonyl, cyano, carbamoyl, sulfamoyl and acetyl groups;
Aa is chosen from one of the groups (i), (ii), (iii), (iv) and (v),

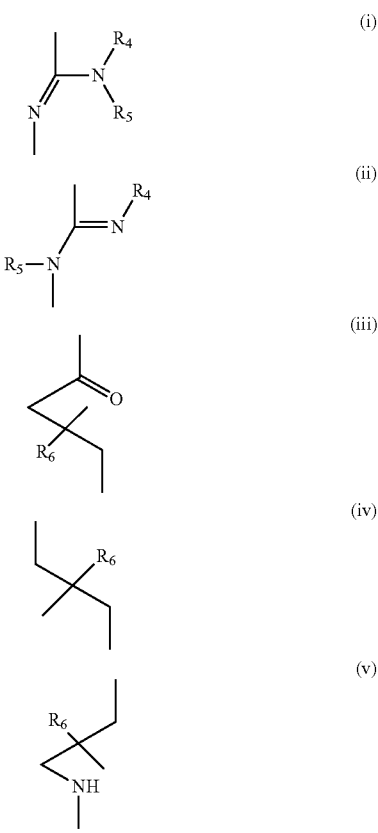

wherein
R$_4$ is chosen from acetamido, dimethylamino, 2,2,2-trifluoroethyl, phenyl, and pyridyl groups; and
R$_5$ is hydrogen; or
R$_4$ and R$_5$ independently of each other are chosen from hydrogen, C$_{1-8}$ branched or unbranched alkyl, and C$_{3-8}$ cycloalkyl groups;
R$_6$ is chosen from hydrogen and C$_{1-3}$ unbranched alkyl groups;
Bb is chosen from sulfonyl and carbonyl groups;
R$_3$ is chosen from pyrrolidinyl, piperidinyl, morpholinyl, naphthyl, benzyl, phenyl, thienyl and pyridyl groups, wherein the benzyl, phenyl, thienyl and pyridyl groups may be substituted with 1, 2 or 3 substituents Y, which can be the same or different;
a prodrug thereof, a tautomer thereof or a pharmaceutically acceptable salt thereof.

8. The method according to claim 7, wherein the subject is further treated with insulin.

9. The method according to claim 7, wherein obese or non-obese subjects with diabetes type I are treated weight-loss independently.

10. The method according to claim 8, wherein obese or non-obese subjects with diabetes type I are treated weight-loss independently.

11. The method according to claim 7, wherein obese or non-obese subjects with diabetes type II are treated weight-loss independently.

12. The method according to claim 8, wherein obese or non-obese subjects with diabetes type II are treated weight-loss independently.

13. The method according to claim 7, wherein the at least one $K_{ATP}$ channel opener and the at least one $CB_1$ antagonist are administered simultaneously, stepwise, or in physical combination.

14. The method according to claim 7, wherein the at least one $K_{ATP}$ channel opener and the at least one $CB_1$ antagonist are administered simultaneously in a fixed combination.

15. The method according to claim 7, wherein the at least one $CB_1$ antagonist or the at least one $K_{ATP}$ channel opener is a dually acting compound comprising combined $K_{ATP}$ channel opening and $CB_1$ antagonistic properties.

16. The method according to claim 1, wherein R is 4-chlorophenyl, $R_1$ is phenyl, $R_2$ is hydrogen, Aa is the group (i) wherein $R_4$ is hydrogen and $R_5$ is methyl, Bb is sulfonyl, and $R_3$ is 4-chlorophenyl in the compound of Formula I, and salts thereof.

17. The method according to claim 1, wherein the compound of Formula I is a levorotatory enantiomer.

18. The method according to claim 1, wherein the compound of Formula I is chosen from
(S)-3-(4-chlorophenyl)-N-[(4-chlorophenyl)sulfonyl]-4,5-dihydro-N'-methyl-4-phenyl-1H-pyrazole-1-carboximidamide;
(−)-3-(4-chlorophenyl)-4,5-dihydro-N-methyl-4-phenyl-N'-(1-piperidinylsulfonyl)-1H-pyrazole-1-carboximidamide, and
(−)-3-(4-chlorophenyl)-4,5-dihydro-4-phenyl-N-methyl-N'-[[4-(trifluoromethyl)-phenyl]sulfonyl]-1H-pyrazole-1-carboximidamide.

19. The method according to claim 6, wherein the dually acting compound comprising combined $K_{ATP}$ channel opening and $CB_1$ antagonistic properties comprises at least one compound chosen from:
(4S)-3-(4-chlorophenyl)-N'-[(4-chlorophenyl)sulfonyl]-N-methyl-4-phenyl-4,5-dihydro-1H-pyrazole-1-carboximidamide;
5-(4-bromophenyl)-1-(2,4-dichlorophenyl)-4-ethyl-N-piperidin-1-yl-1H-pyrazole-3-carboxamide;
5-(1,1-dimethylheptyl)-2-[(1R,2R,5R)-5-hydroxy-2-(3-hydroxypropyl)cyclohexyl]-phenol;
5-(4-chlorophenyl)-1-(2,4-dichlorophenyl)-4-methyl-N-piperidin-1-yl-1H-pyrazole-3-carboxamide;
N'-(azepan-1-ylsulfonyl)-3-(4-chlorophenyl)-N-methyl-4-phenyl-4,5-dihydro-1H-pyrazole-1-carboximidamide;
(2S)-1-[3-(4-chlorophenyl)-4-phenyl-4,5-dihydro-1H-pyrazol-1-yl]-3-(3,4-dichloro-phenyl)-1-oxopropan-2-amine;
3-(4-chlorophenyl)-N'-[(4-chlorophenyl)sulfonyl]-4-phenyl-N-(pyridin-3-ylmethyl)-4,5-dihydro-1H-pyrazole-1-carboximidamide;
(2S)-1-[3-(4-chlorophenyl)-4-phenyl-4,5-dihydro-1H-pyrazol-1-yl]-3-(1H-indol-3-yl)-N-methyl-1-oxopropan-2-amine;
2-[3-(4-chlorophenyl)-4-phenyl-4,5-dihydro-1H-pyrazol-1-yl]-5-ethyl-4,5-dihydro-1,3-oxazole;
3-(4-chlorophenyl)-N-[2-(diethylamino)ethyl]-N'-[(diethylamino)sulfonyl]-4-phenyl-4,5-dihydro-1H-pyrazole-1-carboximidamide;
3-(4-chlorophenyl)-N-[(4-chlorophenyl)sulfonyl]-N'-(3-hydroxy-2,2-dimethylpropyl)-4-phenyl-4,5-dihydro-1H-pyrazole-1-carboximidamide;
3-(4-chlorophenyl)-N-[2-(dimethylamino)ethyl]-4-phenyl-N'-(piperidin-1-ylsulfonyl)-4,5-dihydro-1H-pyrazole-1-carboximidamide;
3-(4-chlorophenyl)-N'-[(4-chlorophenyl)sulfonyl]-N-[(1-methylpyrrolidin-3-yl)methyl]-4-phenyl-4,5-dihydro-1H-pyrazole-1-carboximidamide;
3-(4-chlorophenyl)-N-{[isopropyl(methyl)amino]sulfonyl}-4-phenyl-4,5-dihydro-1H-pyrazole-1-carbothioamide;
5-(4-bromophenyl)-N-[(4-chlorophenyl)sulfonyl]-1-(2,4-dichlorophenyl)-1H-pyrazole-3-carboxamide;
5-(4-bromophenyl)-1-(2,4-dichlorophenyl)-1H-pyrazole-3-carbonitrile;
8-chloro-1-(2,4-dichlorophenyl)-N-piperidin-1-yl-1,4,5,6-tetrahydrobenzo[6,7]cyclo-hepta[1,2-c]pyrazole-3-carboxamide;
3-(4-chlorophenyl)-N'-[(diethylamino)sulfonyl]-4-hydroxy-N-methyl-4-phenyl-4,5-dihydro-1H-pyrazole-1-carboximidamide;
methyl 3-(4-chlorophenyl)-N-[(diethylamino)sulfonyl]-4-phenyl-4,5-dihydro-1H-pyrazole-1-carbimidothioate;
1-[bis(4-chlorophenyl)methyl]-3-[(3,5-difluorophenyl)(methylsulfonyl)methylene]-azetidine;
5-(4-bromophenyl)-1-(2,4-dichlorophenyl)-3-[(Z)-2-(3,5-difluorophenyl)-2-(methyl-sulfonyl)vinyl]-4-methyl-1H-pyrazole;
4-(4-chlorophenyl)-5-(2,4-dichlorophenyl)-N-piperidin-1-yl-1,3-thiazole-2-carboxamide;
2-{1-[bis(4-chlorophenyl)methyl]azetidin-3-yl}-1,2-benzisothiazol-3(2H)-one 1,1-dioxide;
5-(4-chlorophenyl)-4-(2,4-dichlorophenyl)-N-piperidin-1-yl-1,3-thiazole-2-carboxamide;
1-(4-bromophenyl)-N-cyclohexyl-2-(2,4-dichlorophenyl)-5-ethyl-1H-imidazole-4-carboxamide;
1-(4-bromophenyl)-2-(2,4-dichlorophenyl)-5-ethyl-N-pentyl-1H-imidazole-4-carboxamide;
5-(4-chlorophenyl)-1-(2,4-dichlorophenyl)-N-pyrrolidin-1-yl-1H-1,2,4-triazole-3-carboxamide;
3-(4-chlorophenyl)-N'-[(4-hydroxypiperidin-1-yl)sulfonyl]-N-methyl-4-phenyl-4,5-dihydro-1H-pyrazole-1-carboximidamide;
3-(4-chlorophenyl)-N'-[(dimethylamino)sulfonyl]-N-(2-fluoroethyl)-4-phenyl-4,5-dihydro-1H-pyrazole-1-carboximidamide;
1-(4-chlorophenyl)-5-(2,4-dichlorophenyl)-N-piperidin-1-yl-1H-1,2,4-triazole-3-carboxamide;
1-(4-chlorophenyl)-5-(2,4-dichlorophenyl)-N-morpholin-4-yl-1H-1,2,4-triazole-3-carboxamide;
3-(4-chlorophenyl)-4-(3-fluorophenyl)-N-methyl-N'-(piperidin-1-ylsulfonyl)-4,5-dihydro-1H-pyrazole-1-carboximidamide;
3-(4-chlorophenyl)-N-methyl-N'-(morpholin-4-ylsulfonyl)-4-phenyl-4,5-dihydro-1H-pyrazole-1-carboximidamide;
4-(4-chlorophenyl)-N-cyclohexyl-5-(2,4-dichlorophenyl)-1-methyl-1H-imidazole-2-carboxamide;
5-(4-chlorophenyl)-N-cyclohexyl-4-(2,4-dichlorophenyl)-1-methyl-1H-imidazole-2-carboxamide;
1-(4-chlorophenyl)-2-(2,4-dichlorophenyl)-N,N-diethyl-1H-imidazole-4-carboxamide;

5-(4-chlorophenyl)-1-(2,4-dichlorophenyl)-N-piperidin-1-yl-4,5-dihydro-1H-pyrazole-3-carboxamide;
3-(4-chlorophenyl)-N'-[(4-chlorophenyl)sulfonyl]-N-methyl-4-pyridin-3-yl-4,5-dihydro-1H-pyrazole-1-carboximidamide;
1-(4-chlorophenyl)-5-phenyl-N-piperidin-1-yl-4,5-dihydro-1H-pyrazole-3-carboxamide;
1-(4-chlorophenyl)-5-phenyl-4,5-dihydro-1H-pyrazole-3-carboximidamide;
1-(4-chlorophenyl)-2-(2,4-dichlorophenyl)-N-(4-hydroxycyclohexyl)-5-methyl-1H-imidazole-4-carboxamide;
N-azepan-1-yl-1-(4-chlorophenyl)-2-(2,4-dichlorophenyl)-5-methyl-1H-imidazole-4-carboxamide;
2-(2,5-dichlorophenyl)-5-ethyl-1-phenyl-N-piperidin-1-yl-1H-imidazole-4-carboxamide;
N-cyclohexyl-2-(1,5-dimethyl-1H-pyrrol-2-yl)-5-ethyl-1-phenyl-1H-imidazole-4-carboxamide;
1-(4-chlorophenyl)-N-methyl-5-phenyl-N'-(piperidin-1-ylsulfonyl)-4,5-dihydro-1H-pyrazole-3-carboximidamide;
1-(4-chlorophenyl)-N-cyclohexyl-5-ethyl-2-(3-methylpyridin-2-yl)-1H-imidazole-4-carboxamide;
1-(4-chlorophenyl)-5-ethyl-2-(3-methylpyridin-2-yl)-N-piperidin-1-yl-1H-imidazole-4-carboxamide;
1-(4-chlorophenyl)-2-(2,4-dichlorophenyl)-5-methyl-N-[4-(trifluoromethyl)benzyl]-1H-imidazole-4-carboxamide;
2-(2,4-dichlorophenyl)-5-methyl-N-piperidin-1-yl-1-pyridin-2-yl-1H-imidazole-4-carboxamide;
1-(4-bromophenyl)-2-(2,4-dichlorophenyl)-5-ethyl-N-piperidin-1-yl-1H-imidazole-4-carboxamide;
1-(2,4-dichlorophenyl)-N-methyl-N'-(morpholin-4-ylsulfonyl)-5-phenyl-4,5-dihydro-1H-pyrazole-3-carboximidamide;
1-(4-chlorophenyl)-2-(2,4-dichlorophenyl)-5-ethyl-N-piperidin-1-yl-1H-imidazole-4-carboxamide;
1-(4-chlorophenyl)-2-(2,4-dichlorophenyl)-5-(fluoromethyl)-N-piperidin-1-yl-1H-imidazole-4-carboxamide;
1-(4-chlorophenyl)-2-(2,4-dichlorophenyl)-5-(hydroxymethyl)-N-piperidin-1-yl-1H-imidazole-4-carboxamide;
3-(4-chlorophenyl)-N'-[(4-chlorophenyl)sulfonyl]-N-(2-fluoroethyl)-4-phenyl-4,5-dihydro-1H-pyrazole-1-carboximidamide;
1-(4-chlorophenyl)-N-cyclohexyl-2-(2,4-dichlorophenyl)-5-(methylthio)-1H-imidazole-4-carboxamide;
1-(4-chlorophenyl)-2-(2,4-dichlorophenyl)-5-(methylsulfonyl)-N-piperidin-1-yl-1H-imidazole-4-carboxamide;
1-(4-chlorophenyl)-2-(2,4-dichlorophenyl)-5-(methylsulfinyl)-N-piperidin-1-yl-1H-imidazole-4-carboxamide;
3-(4-chlorophenyl)-N-methyl-4-pyridin-3-yl-N'-{[4-(trifluoromethyl)phenyl]sulfonyl}-4,5-dihydro-1H-pyrazole-1-carboximidamide;
5-(4-chlorophenyl)-4-(2,5-dichlorophenyl)-1-methyl-N-piperidin-1-yl-1H-imidazole-2-carboxamide;
2-(2-chlorophenyl)-1-(5-chloropyridin-2-yl)-5-ethyl-N-piperidin-1-yl-1H-imidazole-4-carboxamide;
1-(4-chlorophenyl)-2-(2,4-dichlorophenyl)-N-piperidin-1-yl-5-(2,2,2-trifluoroethyl)-1H-imidazole-4-carboxamide;
1-(5-chloropyridin-2-yl)-2-(2,4-dichlorophenyl)-5-ethyl-N-piperidin-1-yl-1H-imidazole-4-carboxamide;
N-[1-(4-chlorophenyl)-2-(2,4-dichlorophenyl)-5-methyl-1H-imidazol-4-yl]benzamide;
3-(4-chlorophenyl)-N'-[(dimethylamino)sulfonyl]-4-(3-fluorophenyl)-N-methyl-4,5-dihydro-1H-pyrazole-1-carboximidamide;
1-(4-chlorophenyl)-2-(2,4-dichlorophenyl)-N-piperidin-1-yl-5-(pyrrolidin-1-ylmethyl)-1H-imidazole-4-carboxamide;
(4S)-3-(4-chlorophenyl)-N'-[(4-chlorophenyl)sulfonyl]-4-(3-fluorophenyl)-N-methoxy-4,5-dihydro-1H-pyrazole-1-carboximidamide;
N-[5-(4-chlorophenyl)-1-(2,4-dichlorophenyl)-4-methyl-1H-pyrazol-3-yl]piperidine-1-carboxamide;
1-(4-bromophenyl)-5-chloro-2-(2,4-dichlorophenyl)-N-piperidin-1-yl-1H-imidazole-4-carboxamide;
2[1-(4-chlorophenyl)-2-(2,4-dichlorophenyl)-5-methyl-1H-imidazol-4-yl]hexan-2-ol;
(4S)-3-(4-chlorophenyl)-N-methyl-4-phenyl-N'-(piperidin-1-ylsulfonyl)-4,5-dihydro-1H-pyrazole-1-carboximidamide;
N-1-adamantyl-5-pentyl-4-phenyl-1,3-thiazole-2-carboxamide;
1-(4-chlorophenyl)-2-(2,4-dichlorophenyl)-N-piperidin-1-yl-1H-imidazole-4-carboxamide;
N-1-adamantyl-4-pentyl-5-phenyl-1,3-thiazole-2-carboxamide;
1-(4-chlorophenyl)-2-(2,4-dichlorophenyl)-5-methyl-4-pentyl-1H-imidazole;
3-(4-chlorophenyl)-N'-[(4-chlorophenyl)sulfonyl]-4-phenyl-4,5-dihydro-1H-pyrazole-1-carboximidamide;
1-(4-chlorophenyl)-2-(2,4-dichlorophenyl)-5-(ethylthio)-N-piperidin-1-yl-1H-imidazole-4-carboxamide; and
(4S)-3-(4-chlorophenyl)-N'-[(4-chlorophenyl)sulfonyl]-4-phenyl-4,5-dihydro-1H-pyrazole-1-carboximidamide.

20. The method according to claim 19, wherein the dually acting compound comprising combined $K_{ATP}$ channel opening and $CB_1$ antagonistic properties is (4S)-3-(4-chlorophenyl)-N'-[(4-chlorophenyl)sulfonyl]-N-methyl-4-phenyl-4,5-dihydro-1H-pyrazole-1-carboximidamide.

21. The method according to claim 7, wherein R is 4-chlorophenyl, $R_1$ is phenyl, $R_2$ is hydrogen, Aa is the group (i) wherein $R_4$ is hydrogen and $R_5$ is methyl, Bb is sulfonyl, and $R_3$ is 4-chlorophenyl in the compound of Formula I, and salts thereof.

22. The method according to claim 7, wherein the compound of Formula I is a levorotatory enantiomer.

23. The method according to claim 7, wherein the compound of Formula I is chosen from
(S)-3-(4-chlorophenyl)-N-[(4-chlorophenyl)sulfonyl]-4,5-dihydro-N'-methyl-4-phenyl-1H-pyrazole-1-carboximidamide;
(−)-3-(4-chlorophenyl)-4,5-dihydro-N-methyl-4-phenyl-N'-(1-piperidinylsulfonyl)-1H-pyrazole-1-carboximidamide, and
(−)-3-(4-chlorophenyl)-4,5-dihydro-4-phenyl-N-methyl-N'-[[4-(trifluoromethyl)-phenyl]sulfonyl]-1H-pyrazole-1-carboximidamide.

24. The method according to claim 15, wherein the dually acting compound comprising combined $K_{ATP}$ channel opening and $CB_1$ antagonistic properties comprises at least one compound chosen from:
(4S)-3-(4-chlorophenyl)-N'-[(4-chlorophenyl)sulfonyl]-N-methyl-4-phenyl-4,5-dihydro-1H-pyrazole-1-carboximidamide;
5-(4-bromophenyl)-1-(2,4-dichlorophenyl)-4-ethyl-N-piperidin-1-yl-1H-pyrazole-3-carboxamide;
5-(1,1-dimethylheptyl)-2-[(1R,2R,5R)-5-hydroxy-2-(3-hydroxypropyl)cyclohexyl]-phenol;

5-(4-chlorophenyl)-1-(2,4-dichlorophenyl)-4-methyl-N-piperidin-1-yl-1H-pyrazole-3-carboxamide;

N'-(azepan-1-ylsulfonyl)-3-(4-chlorophenyl)-N-methyl-4-phenyl-4,5-dihydro-1H-pyrazole-1-carboximidamide;

(2S)-1-[3-(4-chlorophenyl)-4-phenyl-4,5-dihydro-1H-pyrazol-1-yl]-3-(3,4-dichloro-phenyl)-1-oxopropan-2-amine;

3-(4-chlorophenyl)-N'-[(4-chlorophenyl)sulfonyl]-4-phenyl-N-(pyridin-3-ylmethyl)-4,5-dihydro-1H-pyrazole-1-carboximidamide;

(2S)-1-[3-(4-chlorophenyl)-4-phenyl-4,5-dihydro-1H-pyrazol-1-yl]-3-(1H-indo-3-yl)-N-methyl-1-oxopropan-2-amine;

2-[3-(4-chlorophenyl)-4-phenyl-4,5-dihydro-1H-pyrazol-1-yl]-5-ethyl-4,5-dihydro-1,3-oxazole;

3-(4-chlorophenyl)-N-[2-(diethylamino)ethyl]-N'-[(diethylamino)sulfonyl]-4-phenyl-4,5-dihydro-1H-pyrazole-1-carboximidamide;

3-(4-chlorophenyl)-N-[(4-chlorophenyl)sulfonyl]-N'-(3-hydroxy-2,2-dimethylpropyl)-4-phenyl-4,5-dihydro-1H-pyrazole-1-carboximidamide;

3-(4-chlorophenyl)-N-[2-(dimethylamino)ethyl]-4-phenyl-N'-(piperidin-1-ylsulfonyl)-4,5-dihydro-1H-pyrazole-1-carboximidamide;

3-(4-chlorophenyl)-N'-[(4-chlorophenyl)sulfonyl]-N-[(1-methylpyrrolidin-3-yl)methyl]-4-phenyl-4,5-dihydro-1H-pyrazole-1-carboximidamide;

3-(4-chlorophenyl)-N-{[isopropyl(methyl)amino]sulfonyl}-4-phenyl-4,5-dihydro-1H-pyrazole-1-carbothioamide;

5-(4-bromophenyl)-N-[(4-chlorophenyl)sulfonyl]-1-(2,4-dichlorophenyl)-1H-pyrazole-3-carboxamide;

5-(4-bromophenyl)-1-(2,4-dichlorophenyl)-1H-pyrazole-3-carbonitrile;

8-chloro-1-(2,4-dichlorophenyl)-N-piperidin-1-yl-1,4,5,6-tetrahydrobenzo[6,7]cyclo-hepta[1,2-c]pyrazole-3-carboxamide;

3-(4-chlorophenyl)-N'-[(diethylamino)sulfonyl]-4-hydroxy-N-methyl-4-phenyl-4,5-dihydro-1H-pyrazole-1-carboximidamide;

methyl 3-(4-chlorophenyl)-N-[(diethylamino)sulfonyl]-4-phenyl-4,5-dihydro-1H-pyrazole-1-carbimidothioate;

1-[bis(4-chlorophenyl)methyl]-3-[(3,5-difluorophenyl)(methylsulfonyl)methylene]-azetidine;

5-(4-bromophenyl)-1-(2,4-dichlorophenyl)-3-[(Z)-2-(3,5-difluorophenyl)-2-(methyl-sulfonyl)vinyl]-4-methyl-1H-pyrazole;

4-(4-chlorophenyl)-5-(2,4-dichlorophenyl)-N-piperidin-1-yl-1,3-thiazole-2-carboxamide;

2-{1-[bis(4-chlorophenyl)methyl]azetidin-3-yl}-1,2-benzisothiazol-3(2H)-one 1,1-dioxide;

5-(4-chlorophenyl)-4-(2,4-dichlorophenyl)-N-piperidin-1-yl-1,3-thiazole-2-carboxamide;

1-(4-bromophenyl)-N-cyclohexyl-2-(2,4-dichlorophenyl)-5-ethyl-1H-imidazole-4-carboxamide;

1-(4-bromophenyl)-2-(2,4-dichlorophenyl)-5-ethyl-N-pentyl-1H-imidazole-4-carboxamide;

5-(4-chlorophenyl)-1-(2,4-dichlorophenyl)-N-pyrrolidin-1-yl-1H-1,2,4-triazole-3-carboxamide;

3-(4-chlorophenyl)-N'-[(4-hydroxypiperidin-1-yl)sulfonyl]-N-methyl-4-phenyl-4,5-dihydro-1H-pyrazole-1-carboximidamide;

3-(4-chlorophenyl)-N'-[(dimethylamino)sulfonyl]-N-(2-fluoroethyl)-4-phenyl-4,5-dihydro-1H-pyrazole-1-carboximidamide;

1-(4-chlorophenyl)-5-(2,4-dichlorophenyl)-N-piperidin-1-yl-1H-1,2,4-triazole-3-carboxamide;

1-(4-chlorophenyl)-5-(2,4-dichlorophenyl)-N-morpholin-4-yl-1H-1,2,4-triazole-3-carboxamide;

3-(4-chlorophenyl)-4-(3-fluorophenyl)-N-methyl-N'-(piperidin-1-ylsulfonyl)-4,5-dihydro-1H-pyrazole-1-carboximidamide;

3-(4-chlorophenyl)-N-methyl-N'-(morpholin-4-ylsulfonyl)-4-phenyl-4,5-dihydro-1H-pyrazole-1-carboximidamide;

4-(4-chlorophenyl)-N-cyclohexyl-5-(2,4-dichlorophenyl)-1-methyl-1H-imidazole-2-carboxamide;

5-(4-chlorophenyl)-N-cyclohexyl-4-(2,4-dichlorophenyl)-1-methyl-1H-imidazole-2-carboxamide;

1-(4-chlorophenyl)-2-(2,4-dichlorophenyl)-N,N-diethyl-1H-imidazole-4-carboxamide;

5-(4-chlorophenyl)-1-(2,4-dichlorophenyl)-N-piperidin-1-yl-4,5-dihydro-1H-pyrazole-3-carboxamide;

3-(4-chlorophenyl)-N'-[(4-chlorophenyl)sulfonyl]-N-methyl-4-pyridin-3-yl-4,5-dihydro-1H-pyrazole-1-carboximidamide;

1-(4-chlorophenyl)-5-phenyl-N-piperidin-1-yl-4,5-dihydro-1H-pyrazole-3-carboxamide;

1-(4-chlorophenyl)-5-phenyl-4,5-dihydro-1H-pyrazole-3-carboximidamide;

1-(4-chlorophenyl)-2-(2,4-dichlorophenyl)-N-(4-hydroxycyclohexyl)-5-methyl-1H-imidazole-4-carboxamide;

N-azepan-1-yl-1-(4-chlorophenyl)-2-(2,4-dichlorophenyl)-5-methyl-1H-imidazole-4-carboxamide;

2-(2,5-dichlorophenyl)-5-ethyl-1-phenyl-N-piperidin-1-yl-1H-imidazole-4-carboxamide;

N-cyclohexyl-2-(1,5-dimethyl-1H-pyrrol-2-yl)-5-ethyl-1-phenyl-1H-imidazole-4-carboxamide;

1-(4-chlorophenyl)-N-methyl-5-phenyl-N'-(piperidin-1-ylsulfonyl)-4,5-dihydro-1H-pyrazole-3-carboximidamide;

1-(4-chlorophenyl)-N-cyclohexyl-5-ethyl-2-(3-methylpyridin-2-yl)-1H-imidazole-4-carboxamide;

1-(4-chlorophenyl)-5-ethyl-2-(3-methylpyridin-2-yl)-N-piperidin-1-yl-1H-imidazole-4-carboxamide;

1-(4-chlorophenyl)-2-(2,4-dichlorophenyl)-5-methyl-N-[4-(trifluoromethyl)benzyl]-1H-imidazole-4-carboxamide;

2-(2,4-dichlorophenyl)-5-methyl-N-piperidin-1-yl-1-pyridin-2-yl-1H-imidazole-4-carboxamide;

1-(4-bromophenyl)-2-(2,4-dichlorophenyl)-5-ethyl-N-piperidin-1-yl-1H-imidazole-4-carboxamide;

1-(2,4-dichlorophenyl)-N-methyl-N'-(morpholin-4-ylsulfonyl)-5-phenyl-4,5-dihydro-1H-pyrazole-3-carboximidamide;

1-(4-chlorophenyl)-2-(2,4-dichlorophenyl)-5-ethyl-N-piperidin-1-yl-1H-imidazole-4-carboxamide;

1-(4-chlorophenyl)-2-(2,4-dichlorophenyl)-5-(fluoromethyl)-N-piperidin-1-yl-1H-imidazole-4-carboxamide;

1-(4-chlorophenyl)-2-(2,4-dichlorophenyl)-5-(hydroxymethyl)-N-piperidin-1-yl-1H-imidazole-4-carboxamide;

3-(4-chlorophenyl)-N'-[(4-chlorophenyl)sulfonyl]-N-(2-fluoroethyl)-4-phenyl-4,5-dihydro-1H-pyrazole-1-carboximidamide;

1-(4-chlorophenyl)-N-cyclohexyl-2-(2,4-dichlorophenyl)-5-(methylthio)-1H-imidazole-4-carboxamide;

1-(4-chlorophenyl)-2-(2,4-dichlorophenyl)-5-(methylsulfonyl)-N-piperidin-1-yl-1H-imidazole-4-carboxamide;

1-(4-chlorophenyl)-2-(2,4-dichlorophenyl)-5-(methylsulfinyl)-N-piperidin-1-yl-1H-imidazole-4-carboxamide;

3-(4-chlorophenyl)-N-methyl-4-pyridin-3-yl-N'-{[4-(trifluoromethyl)phenyl]sulfonyl}-4,5-dihydro-1H-pyrazole-1-carboximidamide;
5-(4-chlorophenyl)-4-(2,5-dichlorophenyl)-1-methyl-N-piperidin-1-yl-1H-imidazole-2-carboxamide;
2-(2-chlorophenyl)-1-(5-chloropyridin-2-yl)-5-ethyl-N-piperidin-1-yl-1H-imidazole-4-carboxamide;
1-(4-chlorophenyl)-2-(2,4-dichlorophenyl)-N-piperidin-1-yl-5-(2,2,2-trifluoroethyl)-1H-imidazole-4-carboxamide;
1-(5-chloropyridin-2-yl)-2-(2,4-dichlorophenyl)-5-ethyl-N-piperidin-1-yl-1H-imidazole-4-carboxamide;
N-[1-(4-chlorophenyl)-2-(2,4-dichlorophenyl)-5-methyl-1H-imidazol-4-yl]benzamide;
3-(4-chlorophenyl)-N'-[(dimethylamino)sulfonyl]-4-(3-fluorophenyl)-N-methyl-4,5-dihydro-1H-pyrazole-1-carboximidamide;
1-(4-chlorophenyl)-2-(2,4-dichlorophenyl)-N-piperidin-1-yl-5-(pyrrolidin-1-ylmethyl)-1H-imidazole-4-carboxamide;
(4S)-3-(4-chlorophenyl)-N'-[(4-chlorophenyl)sulfonyl]-4-(3-fluorophenyl)-N-methoxy-4,5-dihydro-1H-pyrazole-1-carboximidamide;
N-[5-(4-chlorophenyl)-1-(2,4-dichlorophenyl)-4-methyl-1H-pyrazol-3-yl]piperidine-1-carboxamide;
1-(4-bromophenyl)-5-chloro-2-(2,4-dichlorophenyl)-N-piperidin-1-yl-1H-imidazole-4-carboxamide;
2-[1-(4-chlorophenyl)-2-(2,4-dichlorophenyl)-5-methyl-1H-imidazol-4-yl]hexan-2-ol;
(4S)-3-(4-chlorophenyl)-N-methyl-4-phenyl-N'-(piperidin-1-ylsulfonyl)-4,5-dihydro-1H-pyrazole-1-carboximidamide;
N-1-adamantyl-5-pentyl-4-phenyl-1,3-thiazole-2-carboxamide;
1-(4-chlorophenyl)-2-(2,4-dichlorophenyl)-N-piperidin-1-yl-1H-imidazole-4-carboxamide;
N-1-adamantyl-4-pentyl-5-phenyl-1,3-thiazole-2-carboxamide;
1-(4-chlorophenyl)-2-(2,4-dichlorophenyl)-5-methyl-4-pentyl-1H-imidazole;
3-(4-chlorophenyl)-N'-[(4-chlorophenyl)sulfonyl]-4-phenyl-4,5-dihydro-1H-pyrazole-1-carboximidamide;
1-(4-chlorophenyl)-2-(2,4-dichlorophenyl)-5-(ethylthio)-N-piperidin-1-yl-1H-imidazole-4-carboxamide; and
(4S)-3-(4-chlorophenyl)-N'-[(4-chlorophenyl)sulfonyl]-4-phenyl-4,5-dihydro-1H-pyrazole-1-carboximidamide.

25. The method according to claim 24, wherein the dually acting compound comprising combined $K_{ATP}$ channel opening and $CB_1$ antagonistic properties is (4S)-3-(4-chlorophenyl)-N'-[(4-chlorophenyl)sulfonyl]-N-methyl-4-phenyl-4,5-dihydro-1H-pyrazole-1-carboximidamide.

* * * * *

UNITED STATES PATENT AND TRADEMARK OFFICE
CERTIFICATE OF CORRECTION

| | | |
|---|---|---|
| PATENT NO. | : 8,058,264 B2 | Page 1 of 1 |
| APPLICATION NO. | : 11/257056 | |
| DATED | : November 15, 2011 | |
| INVENTOR(S) | : Michael Firnges et al. | |

It is certified that error appears in the above-identified patent and that said Letters Patent is hereby corrected as shown below:

Title page, item (54), line 2 of Title, "CB1" should read --$CB_1$--.

Title page, item (75), line 3 of Inventors, "Jochen Antel, Münder (DE);" should read -- Jochen Antel, Bad Münder (DE);--.

Signed and Sealed this

Fourteenth Day of February, 2012

David J. Kappos
*Director of the United States Patent and Trademark Office*

UNITED STATES PATENT AND TRADEMARK OFFICE
CERTIFICATE OF CORRECTION

PATENT NO. : 8,058,264 B2  
APPLICATION NO. : 11/257056  
DATED : November 15, 2011  
INVENTOR(S) : Michael Firnges et al.

Page 1 of 1

It is certified that error appears in the above-identified patent and that said Letters Patent is hereby corrected as shown below:

Title page, item (54) and at Column 1, line 2, in the title, "CB1" should read --$CB_1$--.

Title page, item (75), line 3 of Inventors, "Jochen Antel, Münder (DE);" should read --Jochen Antel, Bad Münder (DE);--.

This certificate supersedes the Certificate of Correction issued February 14, 2012.

Signed and Sealed this  
Twentieth Day of March, 2012

David J. Kappos  
*Director of the United States Patent and Trademark Office*